US008653050B2

(12) United States Patent
Takeuchi et al.

(10) Patent No.: US 8,653,050 B2
(45) Date of Patent: Feb. 18, 2014

(54) PHENYL BICYCLIC METHYL AMINE DERIVATIVES AS SPHINGOSINE-1 PHOSPHATE RECEPTORS MODULATORS

(71) Applicant: Allergan, Inc., Irvine, CA (US)

(72) Inventors: Janet A. Takeuchi, Anaheim, CA (US); Ling Li, Irvine, CA (US); Wha-Bin Im, Irvine, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 13/936,891

(22) Filed: Jul. 8, 2013

(65) Prior Publication Data

US 2013/0338108 A1    Dec. 19, 2013

Related U.S. Application Data

(62) Division of application No. 13/446,352, filed on Apr. 13, 2012, now Pat. No. 8,541,582.

(60) Provisional application No. 61/475,352, filed on Apr. 14, 2011.

(51) Int. Cl.

| | | |
|---|---|---|
| A61K 31/675 | (2006.01) | |
| A61K 31/47 | (2006.01) | |
| A61K 31/662 | (2006.01) | |
| A61P 1/00 | (2006.01) | |
| A61P 5/00 | (2006.01) | |
| A61P 9/10 | (2006.01) | |
| A61P 11/06 | (2006.01) | |
| A61P 13/12 | (2006.01) | |
| A61P 17/00 | (2006.01) | |
| A61P 17/02 | (2006.01) | |
| A61P 17/06 | (2006.01) | |
| A61P 19/02 | (2006.01) | |
| A61P 19/10 | (2006.01) | |
| A61P 21/04 | (2006.01) | |
| A61P 25/00 | (2006.01) | |
| A61P 25/28 | (2006.01) | |
| A61P 27/02 | (2006.01) | |
| A61P 27/06 | (2006.01) | |
| A61P 29/00 | (2006.01) | |
| A61P 31/00 | (2006.01) | |
| A61P 35/04 | (2006.01) | |
| A61P 37/06 | (2006.01) | |
| A61P 37/08 | (2006.01) | |

(52) U.S. Cl.
USPC .............................. 514/82; 514/114; 514/311

(58) Field of Classification Search
None
See application file for complete search history.

(56) References Cited

U.S. PATENT DOCUMENTS

2005/0020837 A1  1/2005 Doherty et al.
2011/0105432 A1  5/2011 Habashita et al.
2011/0230463 A1  9/2011 Harada et al.

FOREIGN PATENT DOCUMENTS

| WO | 03-061567 | 7/2003 |
| WO | 03-062248 | 7/2003 |
| WO | 2005-020882 | 3/2005 |

OTHER PUBLICATIONS

Cross, LC, Rules for the Nomenclature of Organic Chemistry Section E: Sterochemistry, Pure & Appl. Chem., 1976, 11-30, 45.
Hale, Jeffrey J., Potent S1P receptor agonists replicate the pharmacologic actions of the novel immune modulator FTY720, Bioorganic & Medicinal Chemistry Letters, 2004, 3351-3355, 14.
Hale, Jeffrey J., Selecting against SIP3 enhances the acute cardiovascular tolerability of 3-(N-benzyl) aminopropylphosphonic acid SIP receptor agonists, Bioorganic & Medicinal Chemistry Letters, 2004, 3501-3505, 14, US.
Nakade, Shinji et al, Compound Capable of Binding S1P Receptor and Pharmaceutical use Thereof, Database CA Chemical Abstracts Service, Mar. 10, 2005, 13 pages, STN No. 2005:216595.
Stahl, Heinrich et al, Handbook of Pharmaceutical Salts, Verlag Helvetica Chimica Acta—Zurich, 2002, 329-345.

*Primary Examiner* — Janet L Andres
*Assistant Examiner* — Timothy R Rozof
(74) *Attorney, Agent, or Firm* — Doina G. Ene

(57) ABSTRACT

The present invention relates to novel phenyl bicyclic methyl amine derivatives, processes for preparing them, pharmaceutical compositions containing them and their use as pharmaceuticals as modulators of sphingosine-1-phosphate receptors.

10 Claims, 2 Drawing Sheets

PHENYL BICYCLIC METHYL AMINE DERIVATIVES AS SPHINGOSINE-1 PHOSPHATE RECEPTORS MODULATORS

RELATED APPLICATION

This application is a divisional application of U.S. Non-Provisional patent application Ser. No. 13/446,352, filed Apr. 13, 2012, which claims the benefit of U.S. Provisional Application Ser. No. 61/475,352, filed Apr. 14, 2011, all of which are incorporated herein by reference in their entirety.

FIELD OF THE INVENTION

The present invention relates to novel phenyl bicyclic methyl amine derivatives, processes for preparing them, pharmaceutical compositions containing them and their use as pharmaceuticals as modulators of sphingosine-1-phosphate receptors. The invention relates specifically to the use of these compounds and their pharmaceutical compositions to treat disorders associated with sphingosine-1-phosphate (S1P) receptor modulation.

BACKGROUND OF THE INVENTION

Sphingosine-1 phosphate is stored in relatively high concentrations in human platelets, which lack the enzymes responsible for its catabolism, and it is released into the blood stream upon activation of physiological stimuli, such as growth factors, cytokines, and receptor agonists and antigens. It may also have a critical role in platelet aggregation and thrombosis and could aggravate cardiovascular diseases. On the other hand the relatively high concentration of the metabolite in high-density lipoproteins (HDL) may have beneficial implications for atherogenesis. For example, there are recent suggestions that sphingosine-1-phosphate, together with other lysolipids such as sphingosylphosphorylcholine and lysosulfatide, are responsible for the beneficial clinical effects of HDL by stimulating the production of the potent antiatherogenic signaling molecule nitric oxide by the vascular endothelium. In addition, like lysophosphatidic acid, it is a marker for certain types of cancer, and there is evidence that its role in cell division or proliferation may have an influence on the development of cancers. These are currently topics that are attracting great interest amongst medical researchers, and the potential for therapeutic intervention in sphingosine-1-phosphate metabolism is under active investigation.

SUMMARY OF THE INVENTION

We have now discovered a group of novel compounds which are potent and selective sphingosine-1-phosphate modulators. As such, the compounds described herein are useful in treating a wide variety of disorders associated with modulation of sphingosine-1-phosphate receptors. The term "modulator" as used herein, includes but is not limited to: receptor agonist, antagonist, inverse agonist, inverse antagonist, partial agonist, partial antagonist.

This invention describes compounds of Formula I, which have sphingosine-1-phosphate receptor biological activity. The compounds in accordance with the present invention are thus of use in medicine, for example in the treatment of humans with diseases and conditions that are alleviated by S1P modulation.

In one aspect, the invention provides a compound having Formula I or a pharmaceutically acceptable salt thereof or stereoisomeric forms thereof, or the geometrical isomers, enantiomers, diastereoisomers, tautomers, zwitterions and pharmaceutically acceptable salts thereof:

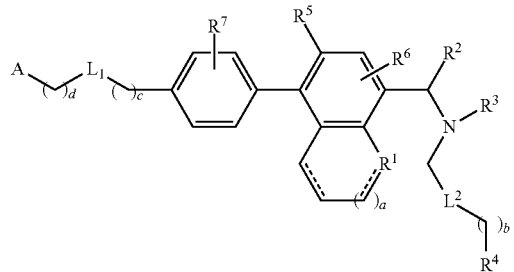

Formula I wherein:

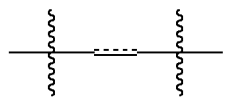

represents a single

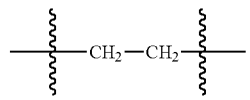

or a double bond

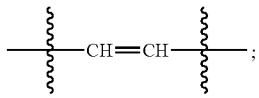

A is substituted or unsubstituted aryl, substituted or unsubstituted heterocycle, substituted or unsubstituted $C_{5-8}$ cycloalkyl, substituted or unsubstituted $C_{5-8}$ cycloalkenyl or hydrogen;

$R^2$ is hydrogen, halogen, —$OC_{1-3}$ alkyl, substituted or unsubstituted $C_{1-3}$ alkyl, CN, C(O)$R^8$, $NR^9R^{10}$ or hydroxyl;

$R^3$ is hydrogen, halogen, substituted or unsubstituted $C_{1-3}$ alkyl, C(O)$R^8$ or hydroxyl;

$R^4$ is $OPO_3H_2$, carboxylic acid, $PO_3H_2$, substituted or unsubstituted $C_{1-6}$ alkyl, —$S(O)_2H$, —$P(O)MeOH$, —$P(O)(H)OH$ or $OR^{11}$;

$R^5$ is H, halogen, —$OC_{1-3}$ alkyl, substituted or unsubstituted $C_{1-3}$ alkyl, CN, C(O)$R^8$, $NR^9R^{10}$ or hydroxyl;

$R^6$ is H, halogen, —$OC_{1-3}$ alkyl, substituted or unsubstituted $C_{1-3}$ alkyl, CN, C(O)$R^8$, $NR^9R^{10}$ or hydroxyl;

$R^7$ is H, halogen, —$OC_{1-3}$ alkyl, substituted or unsubstituted $C_{1-3}$ alkyl, CN, C(O)$R^8$, $NR^9R^{10}$ or hydroxyl;

$R^8$ is H, $OR^{11}$ or substituted or unsubstituted $C_{1-3}$ alkyl;

$R^9$ is H or substituted or unsubstituted $C_{1-3}$ alkyl;

$R^{10}$ is H or substituted or unsubstituted $C_{1-3}$ alkyl;

$R^{11}$ is H or substituted or unsubstituted $C_{1-3}$ alkyl;

$L^1$ is O, S, NH or $CHR^{12}$;

$L^2$ is O, S, NH or $CHR^{13}$;

$R^{12}$ is H or substituted or unsubstituted $C_{1-3}$ alkyl;

$R^{13}$ is H or substituted or unsubstituted $C_{1-3}$ alkyl;

a is 0 or 1;

b is 0, 1, 2 or 3;
c is 0, 1, 2, 3 or 4;
d is 1, 2, 3 or 4; with the provisos
when a is 1 then

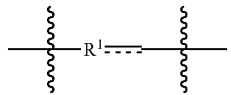

represents

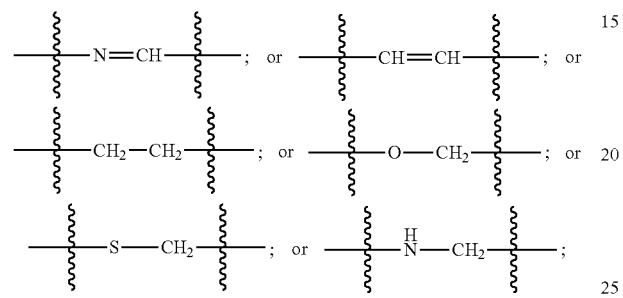

and
when a is 0 then $R^1$ is O, S, NH, or $CH_2$.

In another embodiment, the invention provides a compound having Formula I wherein:

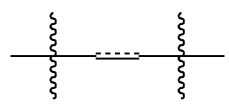

represents a single

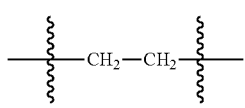

or a double bond

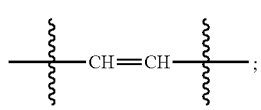

A is substituted or unsubstituted aryl, substituted or unsubstituted heterocycle, substituted or unsubstituted $C_{6-6}$ cycloalkyl, or unsubstituted $C_{5-8}$ cycloalkenyl, or hydrogen;
$R^2$ is hydrogen, halogen, $-OC_{1-3}$ alkyl, substituted or unsubstituted $C_{1-3}$ alkyl, CN, C(O)$R^8$, $NR^9R^{10}$ or hydroxyl;
$R^3$ is hydrogen, halogen, substituted or unsubstituted $C_{1-3}$ alkyl, C(O)$R^8$ or hydroxyl;
$R^4$ is $OPO_3H_2$, carboxylic acid, $PO_3H_2$, substituted or unsubstituted $C_{1-6}$ alkyl, $-S(O)_2H$, $-P(O)MeOH$, $-P(O)(H)OH$ or $OR^{11}$;
$R^5$ is H, halogen, $-OC_{1-3}$ alkyl, substituted or unsubstituted $C_{1-3}$ alkyl, CN, C(O)$R^8$, $NR^9R^{10}$ or hydroxyl;

$R^6$ is H, halogen, $-OC_{1-3}$ alkyl, substituted or unsubstituted $C_{1-3}$ alkyl, CN, C(O)$R^8$, $NR^9R^{10}$ or hydroxyl;
$R^7$ is H, halogen, $-OC_{1-3}$ alkyl, substituted or unsubstituted $C_{1-3}$ alkyl, CN, C(O)$R^8$, $NR^9R^{10}$ or hydroxyl;
$R^8$ is H, $OR^{11}$ or substituted or unsubstituted $C_{1-3}$ alkyl;
$R^9$ is H or substituted or unsubstituted $C_{1-3}$ alkyl;
$R^{10}$ is H or substituted or unsubstituted $C_{1-3}$ alkyl;
$R^{11}$ is H or substituted or unsubstituted $C_{1-3}$ alkyl;
$L^1$ is O, S, NH or $CHR^{12}$;
$L^2$ is O, S, NH or $CHR^{13}$;
$R^{12}$ is H or substituted or unsubstituted $C_{1-3}$ alkyl;
$R^{13}$ is H or substituted or unsubstituted $C_{1-3}$ alkyl;
a is 1;
b is 0, 1, 2 or 3;
c is 0, 1, 2, 3 or 4;
d is 1, 2, 3 or 4;

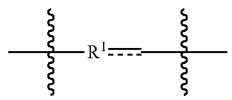

represents

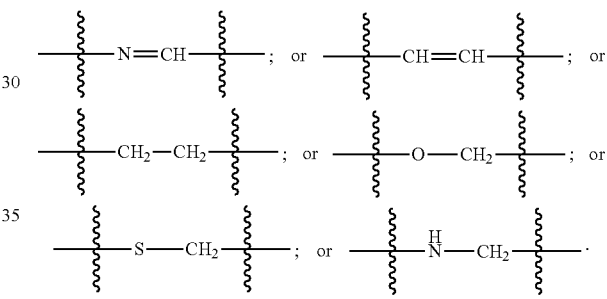

In another embodiment, the invention provides a compound having Formula I wherein:

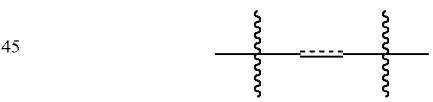

represents or a double bond

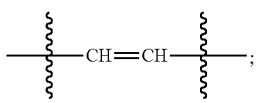 [SMILES: *C=C*]

A is substituted or unsubstituted aryl, substituted or unsubstituted heterocycle, substituted or unsubstituted $C_{5-8}$ cycloalkyl, or unsubstituted $C_{5-8}$ cycloalkenyl, or hydrogen;
$R^2$ is hydrogen, halogen, $-OC_{1-3}$ alkyl, substituted or unsubstituted $C_{1-3}$ alkyl, CN, C(O)$R^8$, $NR^9R^{10}$ or hydroxyl;
$R^3$ is hydrogen, halogen, substituted or unsubstituted $C_{1-3}$ alkyl, C(O)$R^8$ or hydroxyl;
$R^4$ is $OPO_3H_2$, carboxylic acid, $PO_3H_2$, substituted or unsubstituted $C_{1-6}$ alkyl, $-S(O)_2H$, $-P(O)MeOH$, $-P(O)(H)OH$ or $OR^{11}$;

$R^5$ is H, halogen, —O$C_{1-3}$ alkyl, substituted or unsubstituted $C_{1-3}$ alkyl, CN, C(O)$R^8$, N$R^9R^{10}$ or hydroxyl;
$R^6$ is H, halogen, —O$C_{1-3}$ alkyl, substituted or unsubstituted $C_{1-3}$ alkyl, CN, C(O)$R^8$, N$R^9R^{10}$ or hydroxyl;
$R^7$ is H, halogen, —O$C_{1-3}$ alkyl, substituted or unsubstituted $C_{1-3}$ alkyl, CN, C(O)$R^8$, N$R^9R^{10}$ or hydroxyl;
$R^8$ is H, O$R^{11}$ or substituted or unsubstituted $C_{1-3}$ alkyl;
$R^9$ is H or substituted or unsubstituted $C_{1-3}$ alkyl;
$R^{10}$ is H or substituted or unsubstituted $C_{1-3}$ alkyl;
$R^{11}$ is H or substituted or unsubstituted $C_{1-3}$ alkyl;
$L^1$ is O, S, NH or CH$R^{12}$;
$L^2$ is O, S, NH or CH$R^{13}$;
$R^{12}$ is H or substituted or unsubstituted $C_{1-3}$ alkyl;
$R^{13}$ is H or substituted or unsubstituted $C_{1-3}$ alkyl;
a is 1;
b is 0, 1, 2 or 3;
c is 0, 1, 2, 3 or 4;
d is 1, 2, 3 or 4;

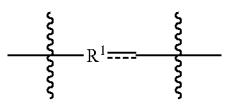

represents

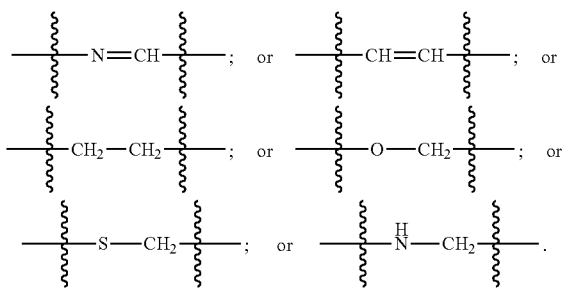

In another embodiment, the invention provides a compound having Formula I wherein:

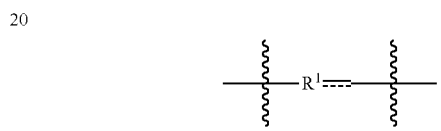

represents a double bond

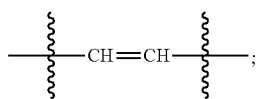 [SMILES: *C=C*]

A is substituted or unsubstituted aryl, substituted or unsubstituted heterocycle, substituted or unsubstituted $C_{5-8}$ cycloalkyl, substituted or unsubstituted $C_{5-8}$ cycloalkenyl, or hydrogen;
$R^2$ is hydrogen, halogen, —O$C_{1-3}$ alkyl, substituted or unsubstituted $C_{1-3}$ alkyl, CN, C(O)$R^8$, N$R^9R^{10}$ or hydroxyl;
$R^3$ is hydrogen, halogen, substituted or unsubstituted $C_{1-3}$ alkyl, C(O)$R^8$ or hydroxyl;
$R^4$ is OPO$_3$H$_2$, carboxylic acid, PO$_3$H$_2$, substituted or unsubstituted $C_{1-6}$ alkyl, —S(O)$_2$H, —P(O)MeOH, —P(O)(H)OH or O$R^{11}$;
$R^5$ is H, halogen, —O$C_{1-3}$ alkyl, substituted or unsubstituted $C_{1-3}$ alkyl, CN, C(O)$R^8$, N$R^9R^{10}$ or hydroxyl;
$R^6$ is H, halogen, —O$C_{1-3}$ alkyl, substituted or unsubstituted $C_{1-3}$ alkyl, CN, C(O)$R^8$, N$R^9R^{10}$ or hydroxyl;
$R^7$ is H, halogen, —O$C_{1-3}$ alkyl, substituted or unsubstituted $C_{1-3}$ alkyl, CN, C(O)$R^8$, N$R^9R^{10}$ or hydroxyl;
$R^8$ is H, O$R^{11}$ or substituted or unsubstituted $C_{1-3}$ alkyl;
$R^9$ is H or substituted or unsubstituted $C_{1-3}$ alkyl;
$R^{10}$ is H or substituted or unsubstituted $C_{1-3}$ alkyl;
$R^{11}$ is H or substituted or unsubstituted $C_{1-3}$ alkyl;
$L^1$ is O, S, NH or CH$R^{12}$;
$L^2$ is O, S, NH or CH$R^{13}$;
$R^{12}$ is H or substituted or unsubstituted $C_{1-3}$ alkyl;
$R^{13}$ is H or substituted or unsubstituted $C_{1-3}$ alkyl;
a is 1;
b is 0, 1, 2 or 3;
c is 0, 1, 2, 3 or 4;
d is 1, 2, 3 or 4;

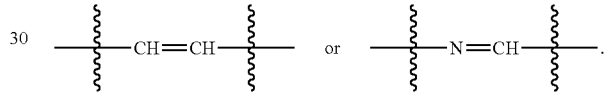

represents

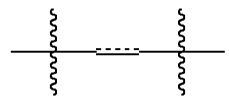

In another embodiment, the invention provides a compound having Formula I wherein:

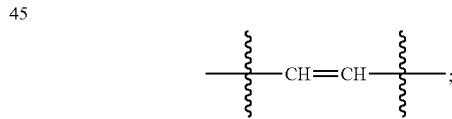

represents a double bond

A is substituted or unsubstituted aryl, substituted or unsubstituted heterocycle, substituted or unsubstituted $C_{5-8}$ cycloalkyl, substituted or unsubstituted $C_{5-8}$ cycloalkenyl, or hydrogen;
$R^2$ is hydrogen, halogen, —O$C_{1-3}$ alkyl, substituted or unsubstituted $C_{1-3}$ alkyl, CN, C(O)$R^8$, N$R^9R^{10}$ or hydroxyl;
$R^3$ is hydrogen, halogen, substituted or unsubstituted $C_{1-3}$ alkyl, C(O)$R^8$ or hydroxyl;
$R^4$ is OPO$_3$H$_2$, carboxylic acid, PO$_3$H$_2$, substituted or unsubstituted $C_{1-6}$ alkyl, —S(O)$_2$H, —P(O)MeOH, —P(O)(H)OH or O$R^{11}$;
$R^5$ is H, halogen, —O$C_{1-3}$ alkyl, substituted or unsubstituted $C_{1-3}$ alkyl, CN, C(O)$R^8$, N$R^9R^{10}$ or hydroxyl;
$R^6$ is H, halogen, —O$C_{1-3}$ alkyl, substituted or unsubstituted $C_{1-3}$ alkyl, CN, C(O)$R^8$, N$R^9R^{10}$ or hydroxyl;
$R^7$ is H, halogen, —O$C_{1-3}$ alkyl, substituted or unsubstituted $C_{1-3}$ alkyl, CN, C(O)$R^8$, N$R^9R^{10}$ or hydroxyl;

$R^8$ is H, $OR^{11}$ or substituted or unsubstituted $C_{1-3}$ alkyl;
$R^9$ is H or substituted or unsubstituted $C_{1-3}$ alkyl;
$R^{10}$ is H or substituted or unsubstituted $C_{1-3}$ alkyl;
$R^{11}$ is H or substituted or unsubstituted $C_{1-3}$ alkyl;
$L^1$ is O, S, NH or $CHR^{12}$;
$L^2$ is O, S, NH or $CHR^{13}$;
$R^{12}$ is H or substituted or unsubstituted $C_{1-3}$ alkyl;
$R^{13}$ is H or substituted or unsubstituted $C_{1-3}$ alkyl;
a is 1;
b is 0, 1, 2 or 3;
c is 0, 1, 2, 3 or 4;
d is 1, 2, 3 or 4; and

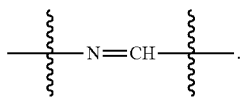 [SMILES: *C=N*]

represents

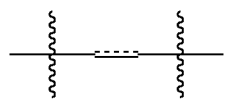

In another embodiment, the invention provides a compound having Formula I wherein:

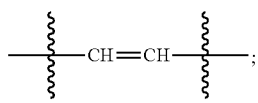 [SMILES: *C=C*]

represents a double bond

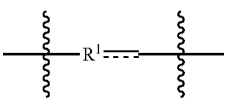

A is substituted or unsubstituted aryl;
$R^2$ is hydrogen, halogen, —$OC_{1-3}$ alkyl, substituted or unsubstituted $C_{1-3}$ alkyl, CN, $C(O)R^8$, $NR^9R^{10}$ or hydroxyl;
$R^3$ is hydrogen, halogen, substituted or unsubstituted $C_{1-3}$ alkyl, $C(O)R^8$ or hydroxyl;
$R^4$ is $OPO_3H_2$, carboxylic acid, $PO_3H_2$, substituted or unsubstituted $C_{1-6}$ alkyl, —$S(O)_2H$, —$P(O)MeOH$, —$P(O)(H)OH$ or $OR^{11}$;
$R^5$ is H, halogen, —$OC_{1-3}$ alkyl, substituted or unsubstituted $C_{1-3}$ alkyl, CN, $C(O)R^8$, $NR^9R^{10}$ or hydroxyl;
$R^6$ is H, halogen, —$OC_{1-3}$ alkyl, substituted or unsubstituted $C_{1-3}$ alkyl, CN, $C(O)R^8$, $NR^9R^{10}$ or hydroxyl;
$R^7$ is H, halogen, —$OC_{1-3}$ alkyl, substituted or unsubstituted $C_{1-3}$ alkyl, CN, $C(O)R^8$, $NR^9R^{10}$ or hydroxyl;
$R^8$ is H, $OR^{11}$ or substituted or unsubstituted $C_{1-3}$ alkyl;
$R^9$ is H or substituted or unsubstituted $C_{1-3}$ alkyl;
$R^{10}$ is H or substituted or unsubstituted $C_{1-3}$ alkyl;
$R^{11}$ is H or substituted or unsubstituted $C_{1-3}$ alkyl;
$L^1$ is O, S, NH or $CHR^{12}$;
$L^2$ is O, S, NH or $CHR^{13}$;
$R^{12}$ is H or substituted or unsubstituted $C_{1-3}$ alkyl;
$R^{13}$ is H or substituted or unsubstituted $C_{1-3}$ alkyl;
a is 1;
b is 0, 1, 2 or 3;
c is 0, 1, 2, 3 or 4;
d is 1, 2, 3 or 4;

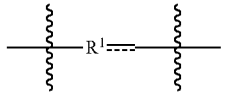

represents

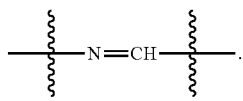

In another embodiment, the invention provides a compound having Formula I wherein:

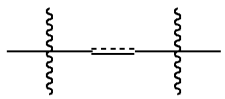

represents a double bond

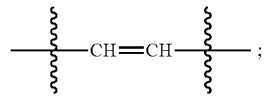 [SMILES: *C=C*]

A is substituted or unsubstituted aryl;
$R^2$ is hydrogen, substituted or unsubstituted $C_{1-3}$ alkyl;
$R^3$ is hydrogen;
$R^4$ is $OPO_3H_2$, carboxylic acid, $PO_3H_2$, or $OR^{11}$;
$R^5$ is H, halogen;
$R^6$ is H, halogen;
$R^7$ is H, halogen;
$R^{11}$ is H or substituted or unsubstituted $C_{1-3}$ alkyl;
$L^1$ is $CHR^{12}$;
$L^2$ is $CHR^{13}$;
$R^{12}$ is H or substituted or unsubstituted $C_{1-3}$ alkyl;
$R^{13}$ is H or substituted or unsubstituted $C_{1-3}$ alkyl;
a is 1;
b is 0, 1;
c is 0, 1, 2, 3 or 4;
d is 1, 2, 3 or 4;

represents

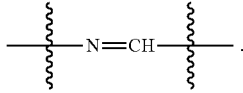 [SMILES: *C=N*]

In another embodiment, the invention provides a compound having Formula I wherein:

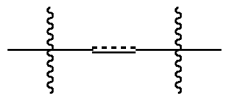

represents a double bond

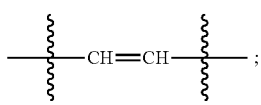 [SMILES: *C=C*]

A is substituted or unsubstituted $C_6$ aryl, substituted or unsubstituted heterocycle, substituted or unsubstituted $C_{6-6}$ cycloalkyl, substituted or unsubstituted $C_{5-8}$ cycloalkenyl, or hydrogen;
$R^2$ is hydrogen, halogen, —$OC_{1-3}$ alkyl, substituted or unsubstituted $C_{1-3}$ alkyl, CN, $C(O)R^8$, $NR^9R^{10}$ or hydroxyl;
$R^3$ is hydrogen, halogen, substituted or unsubstituted $C_{1-3}$ alkyl, $C(O)R^8$ or hydroxyl;
$R^4$ is $OPO_3H_2$, carboxylic acid, $PO_3H_2$, substituted or unsubstituted $C_{1-6}$ alkyl, —$S(O)_2H$, —$P(O)MeOH$, —$P(O)(H)OH$ or $OR^{11}$;
$R^5$ is H, halogen, —$OC_{1-3}$ alkyl, substituted or unsubstituted $C_{1-3}$ alkyl, CN, $C(O)R^8$, $NR^9R^{10}$ or hydroxyl;
$R^6$ is H, halogen, —$OC_{1-3}$ alkyl, substituted or unsubstituted $C_{1-3}$ alkyl, CN, $C(O)R^8$, $NR^9R^{10}$ or hydroxyl;
$R^7$ is H, halogen, —$OC_{1-3}$ alkyl, substituted or unsubstituted $C_{1-3}$ alkyl, CN, $C(O)R^8$, $NR^9R^{10}$ or hydroxyl;
$R^8$ is H, $OR^{11}$ or substituted or unsubstituted $C_{1-3}$ alkyl;
$R^9$ is H or substituted or unsubstituted $C_{1-3}$ alkyl;
$R^{10}$ is H or substituted or unsubstituted $C_{1-3}$ alkyl;
$R^{11}$ is H or substituted or unsubstituted $C_{1-3}$ alkyl;
$L^1$ is O, S, NH or $CHR^{12}$;
$L^2$ is O, S, NH or $CHR^{13}$;
$R^{12}$ is H or substituted or unsubstituted $C_{1-3}$ alkyl;
$R^{13}$ is H or substituted or unsubstituted $C_{1-3}$ alkyl;
a is 1;
b is 0, 1, 2 or 3;
c is 0, 1, 2, 3 or 4;
d is 1, 2, 3 or 4;

"$R^1$====="

represents "—CH=CH—".
In another embodiment, the invention provides a compound having Formula I wherein:

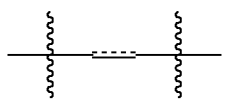

represents a double bond

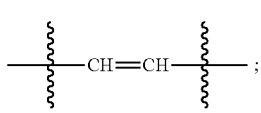 [SMILES: *C=C*]

A is substituted or unsubstituted aryl;
$R^2$ is hydrogen, halogen, —$OC_{1-3}$ alkyl, substituted or unsubstituted $C_{1-3}$ alkyl, CN, $C(O)R^8$, $NR^9R^{10}$ or hydroxyl;
$R^3$ is hydrogen, halogen, substituted or unsubstituted $C_{1-3}$ alkyl, $C(O)R^8$ or hydroxyl;
$R^4$ is $OPO_3H_2$, carboxylic acid, $PO_3H_2$, substituted or unsubstituted $C_{1-6}$ alkyl, —$S(O)_2H$, —$P(O)MeOH$, —$P(O)(H)OH$ or $OR^{11}$;
$R^5$ is H, halogen, —$OC_{1-3}$ alkyl, substituted or unsubstituted $C_{1-3}$ alkyl, CN, $C(O)R^8$, $NR^9R^{10}$ or hydroxyl;
$R^6$ is H, halogen, —$OC_{1-3}$ alkyl, substituted or unsubstituted $C_{1-3}$ alkyl, CN, $C(O)R^8$, $NR^9R^{10}$ or hydroxyl;
$R^7$ is H, halogen, —$OC_{1-3}$ alkyl, substituted or unsubstituted $C_{1-3}$ alkyl, CN, $C(O)R^8$, $NR^9R^{10}$ or hydroxyl;
$R^8$ is H, $OR^{11}$ or substituted or unsubstituted $C_{1-3}$ alkyl;
$R^9$ is H or substituted or unsubstituted $C_{1-3}$ alkyl;
$R^{10}$ is H or substituted or unsubstituted $C_{1-3}$ alkyl;
$R^{11}$ is H or substituted or unsubstituted $C_{1-3}$ alkyl;
$L^1$ is O, S, NH or $CHR^{12}$;
$L^2$ is O, S, NH or $CHR^{13}$;
$R^{12}$ is H or substituted or unsubstituted $C_{1-3}$ alkyl;
$R^{13}$ is H or substituted or unsubstituted $C_{1-3}$ alkyl;
a is 1;
b is 0, 1, 2 or 3;
c is 0, 1, 2, 3 or 4;
d is 1, 2, 3 or 4;

"$R^1$====="

represents "—CH=CH—".
In another embodiment, the invention provides a compound having Formula I wherein:

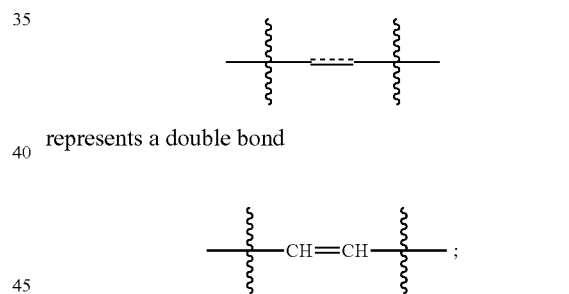

represents a double bond

A is substituted or unsubstituted aryl;
$R^2$ is hydrogen, substituted or unsubstituted $C_{1-3}$ alkyl;
$R^3$ is hydrogen;
$R^4$ is $OPO_3H_2$, carboxylic acid, $PO_3H_2$, or $OR^{11}$;
$R^5$ is H, halogen;
$R^6$ is H, halogen;
$R^7$ is H, halogen;
$R^{11}$ is H or substituted or unsubstituted $C_{1-3}$ alkyl;
$L^1$ is $CHR^{12}$;
$L^2$ is $CHR^{13}$;
$R^{12}$ is H or substituted or unsubstituted $C_{1-3}$ alkyl;
$R^{13}$ is H or substituted or unsubstituted $C_{1-3}$ alkyl;
a is 1;
b is 0, 1;
c is 0, 1, 2, 3 or 4;
d is 1, 2, 3 or 4;

"$R^1$====="

represents "—CH=CH—".

In another embodiment, the invention provides a compound having Formula I wherein:

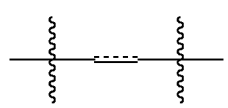

represents a double bond

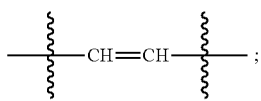 [SMILES: *C=C*]

A is hydrogen;
$R^2$ is hydrogen, halogen, —$OC_{1-3}$ alkyl, substituted or unsubstituted $C_{1-3}$ alkyl, CN, $C(O)R^8$, $NR^9R^{10}$ or hydroxyl;
$R^3$ is hydrogen, halogen, substituted or unsubstituted $C_{1-3}$ alkyl, $C(O)R^8$ or hydroxyl;
$R^4$ is $OPO_3H_2$, carboxylic acid, $PO_3H_2$, substituted or unsubstituted $C_{1-6}$ alkyl, —$S(O)_2H$, —$P(O)MeOH$, —$P(O)(H)OH$ or $OR^{11}$;
$R^5$ is H, halogen, —$OC_{1-3}$ alkyl, substituted or unsubstituted $C_{1-3}$ alkyl, CN, $C(O)R^8$, $NR^9R^{10}$ or hydroxyl;
$R^6$ is H, halogen, —$OC_{1-3}$ alkyl, substituted or unsubstituted $C_{1-3}$ alkyl, CN, $C(O)R^8$, $NR^9R^{10}$ or hydroxyl;
$R^7$ is H, halogen, —$OC_{1-3}$ alkyl, substituted or unsubstituted $C_{1-3}$ alkyl, CN, $C(O)R^8$, $NR^9R^{10}$ or hydroxyl;
$R^8$ is H, $OR^{11}$ or substituted or unsubstituted $C_{1-3}$ alkyl;
$R^9$ is H or substituted or unsubstituted $C_{1-3}$ alkyl;
$R^{10}$ is H or substituted or unsubstituted $C_{1-3}$ alkyl;
$R^{11}$ is H or substituted or unsubstituted $C_{1-3}$ alkyl;
$L^1$ is O, S, NH or $CHR^{12}$;
$L^2$ is O, S, NH or $CHR^{13}$;
$R^{12}$ is H or substituted or unsubstituted $C_{1-3}$ alkyl;
$R^{13}$ is H or substituted or unsubstituted $C_{1-3}$ alkyl;
a is 1;
b is 0, 1, 2 or 3;
c is 0, 1, 2, 3 or 4;
d is 1, 2, 3 or 4;

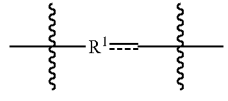

represents

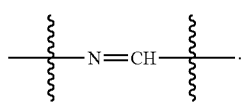 [SMILES: *C=N*]

In another embodiment, the invention provides a compound having Formula I wherein:

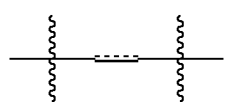

represents a double bond

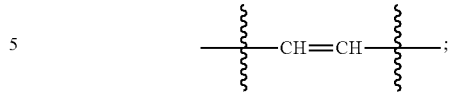

A is hydrogen;
$R^2$ is hydrogen, substituted or unsubstituted $C_{1-3}$ alkyl;
$R^3$ is hydrogen;
$R^4$ is $OPO_3H_2$, carboxylic acid, $PO_3H_2$, or $OR^{11}$;
$R^5$ is H, halogen;
$R^6$ is H, halogen;
$R^7$ is H, halogen;
$R^{11}$ is H or substituted or unsubstituted $C_{1-3}$ alkyl;
$L^1$ is $CHR^{12}$;
$L^2$ is $CHR^{13}$;
$R^{12}$ is H or substituted or unsubstituted $C_{1-3}$ alkyl;
$R^{13}$ is H or substituted or unsubstituted $C_{1-3}$ alkyl;
a is 1;
b is 0, 1;
c is 0, 1, 2, 3 or 4;
d is 1, 2, 3 or 4;

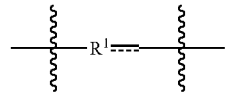

represents

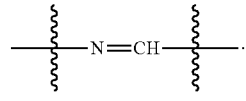

In another embodiment, the invention provides a compound having Formula I wherein:

represents a double bond

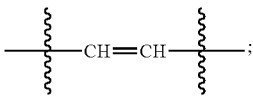 [SMILES: *C=C*]

A is hydrogen;
$R^2$ is hydrogen, halogen, —$OC_{1-3}$ alkyl, substituted or unsubstituted $C_{1-3}$ alkyl, CN, $C(O)R^8$, $NR^9R^{10}$ or hydroxyl;
$R^3$ is hydrogen, halogen, substituted or unsubstituted $C_{1-3}$ alkyl, $C(O)R^8$ or hydroxyl;
$R^4$ is $OPO_3H_2$, carboxylic acid, $PO_3H_2$, substituted or unsubstituted $C_{1-6}$ alkyl, —$S(O)_2H$, —$P(O)MeOH$, —$P(O)(H)OH$ or $OR^{11}$;
$R^5$ is H, halogen, —$OC_{1-3}$ alkyl, substituted or unsubstituted $C_{1-3}$ alkyl, CN, $C(O)R^8$, $NR^9R^{10}$ or hydroxyl;

$R^6$ is H, halogen, —$OC_{1-3}$ alkyl, substituted or unsubstituted $C_{1-3}$ alkyl, CN, $C(O)R^8$, $NR^9R^{10}$ or hydroxyl;
$R^7$ is H, halogen, —$OC_{1-3}$ alkyl, substituted or unsubstituted $C_{1-3}$ alkyl, CN, $C(O)R^8$, $NR^9R^{10}$ or hydroxyl;
$R^8$ is H, $OR^{11}$ or substituted or unsubstituted $C_{1-3}$ alkyl;
$R^9$ is H or substituted or unsubstituted $C_{1-3}$ alkyl;
$R^{10}$ is H or substituted or unsubstituted $C_{1-3}$ alkyl;
$R^{11}$ is H or substituted or unsubstituted $C_{1-3}$ alkyl;
$L^1$ is O, S, NH or $CHR^{12}$;
$L^2$ is O, S, NH or $CHR^{13}$;
$R^{12}$ is H or substituted or unsubstituted $C_{1-3}$ alkyl;
$R^{13}$ is H or substituted or unsubstituted $C_{1-3}$ alkyl;
a is 1;
b is 0, 1, 2 or 3;
c is 0, 1, 2, 3 or 4;
d is 1, 2, 3 or 4;

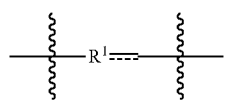

represents

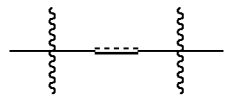

In another embodiment, the invention provides a compound having Formula I wherein:

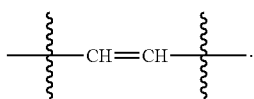

represents a double bond

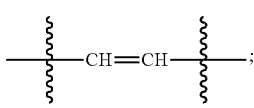 [SMILES: *C=C*]

A is hydrogen;
$R^2$ is hydrogen, substituted or unsubstituted $C_{1-3}$ alkyl;
$R^3$ is hydrogen;
$R^4$ is $OPO_3H_2$, carboxylic acid, $PO_3H_2$, or $OR^{11}$;
$R^5$ is H, halogen;
$R^6$ is H, halogen;
$R^7$ is H, halogen;
$R^{11}$ is H or substituted or unsubstituted $C_{1-3}$ alkyl;
$L^1$ is $CHR^{12}$;
$L^2$ is $CHR^{13}$;
$R^{12}$ is H or substituted or unsubstituted $C_{1-3}$ alkyl;
$R^{13}$ is H or substituted or unsubstituted $C_{1-3}$ alkyl;
a is 1;
b is 0, 1;
c is 0, 1, 2, 3 or 4;
d is 1, 2, 3 or 4;

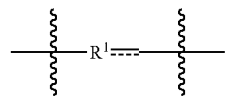

represents

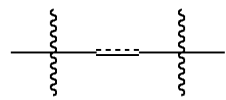

In another embodiment, the invention provides a compound having Formula I wherein:

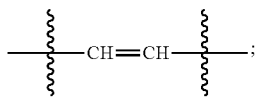

represents a double bond

—CH═CH—;

A is substituted or unsubstituted $C_{5-8}$ cycloalkyl;
$R^2$ is hydrogen, halogen, —$OC_{1-3}$ alkyl, substituted or unsubstituted $C_{1-3}$ alkyl, CN, $C(O)R^8$, $NR^9R^{10}$ or hydroxyl;
$R^3$ is hydrogen, halogen, substituted or unsubstituted $C_{1-3}$ alkyl, $C(O)R^8$ or hydroxyl;
$R^4$ is $OPO_3H_2$, carboxylic acid, $PO_3H_2$, substituted or unsubstituted $C_{1-6}$ alkyl, —$S(O)_2H$, —$P(O)MeOH$, —$P(O)(H)OH$ or $OR^{11}$;
$R^5$ is H, halogen, —$OC_{1-3}$ alkyl, substituted or unsubstituted $C_{1-3}$ alkyl, CN, $C(O)R^8$, $NR^9R^{10}$ or hydroxyl;
$R^6$ is H, halogen, —$OC_{1-3}$ alkyl, substituted or unsubstituted $C_{1-3}$ alkyl, CN, $C(O)R^8$, $NR^9R^{10}$ or hydroxyl;
$R^7$ is H, halogen, —$OC_{1-3}$ alkyl, substituted or unsubstituted $C_{1-3}$ alkyl, CN, $C(O)R^8$, $NR^9R^{10}$ or hydroxyl;
$R^8$ is H, $OR^{11}$ or substituted or unsubstituted $C_{1-3}$ alkyl;
$R^9$ is H or substituted or unsubstituted $C_{1-3}$ alkyl;
$R^{10}$ is H or substituted or unsubstituted $C_{1-3}$ alkyl;
$R^{11}$ is H or substituted or unsubstituted $C_{1-3}$ alkyl;
$L^1$ is O, S, NH or $CHR^{12}$;
$L^2$ is O, S, NH or $CHR^{13}$;
$R^{12}$ is H or substituted or unsubstituted $C_{1-3}$ alkyl;
$R^{13}$ is H or substituted or unsubstituted $C_{1-3}$ alkyl;
a is 1;
b is 0, 1, 2 or 3;
c is 0, 1, 2, 3 or 4;
d is 1, 2, 3 or 4;

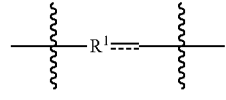

represents

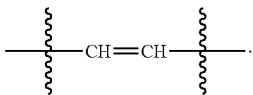

In another embodiment, the invention provides a compound having Formula I wherein:

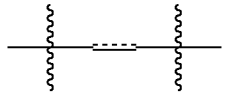

represents a double bond

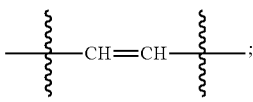 [SMILES: *C=C*]

A is substituted or unsubstituted $C_{5-8}$ cycloalkyl;
$R^2$ is hydrogen, substituted or unsubstituted $C_{1-3}$ alkyl;
$R^3$ is hydrogen;
$R^4$ is $OPO_3H_2$, carboxylic acid, $PO_3H_2$, or $OR^{11}$;
$R^5$ is H, halogen;
$R^6$ is H, halogen;
$R^7$ is H, halogen;
$R^{11}$ is H or substituted or unsubstituted $C_{1-3}$ alkyl;
$L^1$ is $CHR^{12}$;
$L^2$ is $CHR^{13}$;
$R^{12}$ is H or substituted or unsubstituted $C_{1-3}$ alkyl;
$R^{13}$ is H or substituted or unsubstituted $C_{1-3}$ alkyl;
a is 1;
b is 0, 1;
c is 0, 1, 2, 3 or 4;
d is 1, 2, 3 or 4;

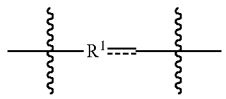

represents

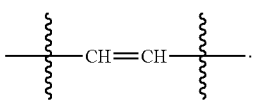

In another embodiment, the invention provides a compound having Formula I wherein:

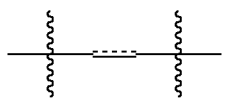

represents a double bond

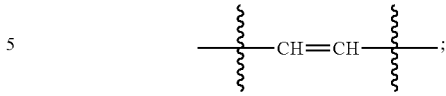

A is substituted or unsubstituted $C_{5-8}$ cycloalkyl;
$R^2$ is hydrogen, halogen, $-OC_{1-3}$ alkyl, substituted or unsubstituted $C_{1-3}$ alkyl, CN, $C(O)R^8$, $NR^9R^{10}$ or hydroxyl;
$R^3$ is hydrogen, halogen, substituted or unsubstituted $C_{1-3}$ alkyl, $C(O)R^8$ or hydroxyl;
$R^4$ is $OPO_3H_2$, carboxylic acid, $PO_3H_2$, substituted or unsubstituted $C_{1-6}$ alkyl, $-S(O)_2H$, $-P(O)MeOH$, $-P(O)(H)OH$ or $OR^{11}$;
$R^5$ is H, halogen, $-OC_{1-3}$ alkyl, substituted or unsubstituted $C_{1-3}$ alkyl, CN, $C(O)R^8$, $NR^9R^{10}$ or hydroxyl;
$R^6$ is H, halogen, $-OC_{1-3}$ alkyl, substituted or unsubstituted $C_{1-3}$ alkyl, CN, $C(O)R^8$, $NR^9R^{10}$ or hydroxyl;
$R^7$ is H, halogen, $-OC_{1-3}$ alkyl, substituted or unsubstituted $C_{1-3}$ alkyl, CN, $C(O)R^8$, $NR^9R^{10}$ or hydroxyl;
$R^8$ is H, $OR^{11}$ or substituted or unsubstituted $C_{1-3}$ alkyl;
$R^9$ is H or substituted or unsubstituted $C_{1-3}$ alkyl;
$R^{10}$ is H or substituted or unsubstituted $C_{1-3}$ alkyl;
$R^{11}$ is H or substituted or unsubstituted $C_{1-3}$ alkyl;
$L^1$ is O, S, NH or $CHR^{12}$;
$L^2$ is O, S, NH or $CHR^{13}$;
$R^{12}$ is H or substituted or unsubstituted $C_{1-3}$ alkyl;
$R^{13}$ is H or substituted or unsubstituted $C_{1-3}$ alkyl;
a is 1;
b is 0, 1, 2 or 3;
c is 0, 1, 2, 3 or 4;
d is 1, 2, 3 or 4;

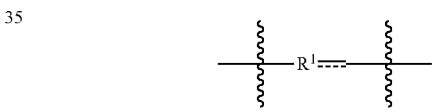

represents

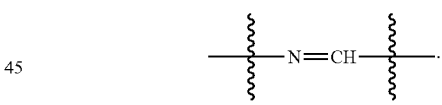

In another embodiment, the invention provides a compound having Formula I wherein:

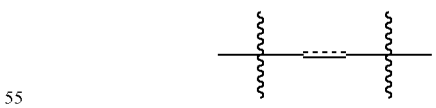

represents a double bond

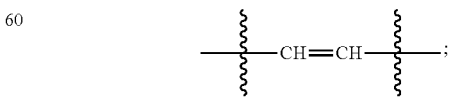

A is substituted or unsubstituted $C_{6-8}$ cycloalkyl;
$R^2$ is hydrogen, substituted or unsubstituted $C_{1-3}$ alkyl;
$R^3$ is hydrogen;

$R^4$ is $OPO_3H_2$, carboxylic acid, $PO_3H_2$, or $OR^{11}$;
$R^5$ is H, halogen;
$R^6$ is H, halogen;
$R^7$ is H, halogen;
$R^{11}$ is H or substituted or unsubstituted $C_{1-3}$ alkyl;
$L^1$ is $CHR^{12}$;
$L^2$ is $CHR^{13}$;
$R^{12}$ is H or substituted or unsubstituted $C_{1-3}$ alkyl;
$R^{13}$ is H or substituted or unsubstituted $C_{1-3}$ alkyl;
a is 1;
b is 0, 1;
c is 0, 1, 2, 3 or 4;
d is 1, 2, 3 or 4;

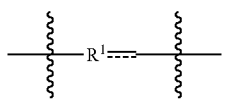

represents

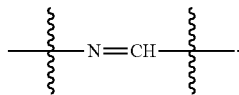 [SMILES: *C=N*]

The term "alkyl", as used herein, refers to saturated, monovalent or divalent hydrocarbon moieties having linear or branched moieties or combinations thereof and containing 1 to 6 carbon atoms. One methylene (—$CH_2$—) group, of the alkyl can be replaced by oxygen, sulfur, sulfoxide, nitrogen, carbonyl, carboxyl, sulfonyl, or by a divalent $C_{3-6}$ cycloalkyl. Alkyl groups can be substituted by halogen, hydroxyl, cycloalkyl, amino, non-aromatic heterocycles, carboxylic acid, phosphonic acid groups, sulphonic acid groups, phosphoric acid.

The term "cycloalkyl", as used herein, refers to a monovalent or divalent group of 3 to 8 carbon atoms, preferably 3 to 5 carbon atoms derived from a saturated cyclic hydrocarbon. Cycloalkyl groups can be monocyclic or polycyclic. Cycloalkyl can be substituted by 1 to 3 $C_{1-3}$ alkyl groups or 1 or 2 halogens.

The term "cycloalkenyl", as used herein, refers to a monovalent or divalent group of 3 to 8 carbon atoms, preferably 3 to 6 carbon atoms derived from a saturated cycloalkyl having one double bond. Cycloalkenyl groups can be monocyclic or polycyclic. Cycloalkenyl groups can be substituted by 1 to 3 $C_{1-3}$ alkyl groups or 1 or 2 halogens.

The term "halogen", as used herein, refers to an atom of chlorine, bromine, fluorine, iodine.

The term "alkenyl", as used herein, refers to a monovalent or divalent hydrocarbon radical having 2 to 6 carbon atoms, derived from a saturated alkyl, having at least one double bond. $C_{2-6}$ alkenyl can be in the E or Z configuration. Alkenyl groups can be substituted by 1 to 2 $C_{1-3}$ alkyl.

The term "alkynyl", as used herein, refers to a monovalent or divalent hydrocarbon radical having 2 to 6 carbon atoms, derived from a saturated alkyl, having at least one triple bond.

The term "heterocycle" as used herein, refers to a 3 to 10 membered ring, which can be aromatic or non-aromatic, saturated or non-saturated, containing at least one heteroatom selected form O or N or S or combinations of at least two thereof, interrupting the carbocyclic ring structure. The heterocyclic ring can be saturated or non-saturated. The heterocyclic ring can be interrupted by a C═O; the S heteroatom can be oxidized. Heterocycles can be monocyclic or polycyclic. Heterocyclic ring moieties can be substituted by hydroxyl, 1 to 2 $C_{1-3}$ alkyl or 1 to 2 halogens. Usually, in the present case, heterocyclic groups are 5 or 6 membered rings. Usually, in the present case, heterocyclic groups are pyridine, furan, azetidine, thiazol, thiophene, oxazol, pyrazol.

The term "aryl" as used herein, refers to an organic moiety derived from an aromatic hydrocarbon consisting of a ring containing 6 to 10 carbon atoms by removal of one hydrogen, which can be substituted by 1 to 3 halogen atoms or by 1 to 2 $C_{1-3}$ alkyl groups. Usually aryl is phenyl. Preferred substitution site on aryl are meta and para positions.

The term "hydroxyl" as used herein, represents a group of formula "—OH".

The term "carbonyl" as used herein, represents a group of formula "—C(O)".

The term "carboxyl" as used herein, represents a group of formula "—C(O)O—".

The term "sulfonyl" as used herein, represents a group of formula "—$SO_2$".

The term "sulfate" as used herein, represents a group of formula "—O—$S(O)_2$—O—".

The term "carboxylic acid" as used herein, represents a group of formula "—C(O)ON".

The term "sulfoxide" as used herein, represents a group of formula "—S═O".

The term "phosphonic acid" as used herein, represents a group of formula "—$P(O)(OH)_2$".

The term "phosphoric acid" as used herein, represents a group of formula "—$(O)P(O)(OH)_2$".

The term "boronic acid", as used herein, represents a group of formula "—$B(OH)_2$".

The term "sulphonic acid" as used herein, represents a group of formula "—$S(O)_2OH$".

The formula "H", as used herein, represents a hydrogen atom.

The formula "O", as used herein, represents an oxygen atom.

The formula "N", as used herein, represents a nitrogen atom.

The formula "S", as used herein, represents a sulfur atom.

Some compounds of the invention are:
[3-({[5-(4-hexylphenyl)quinolin-8-yl]methyl}amino)propyl]phosphonic acid;
[3-({[4-(4-hexylphenyl)-1-naphthyl]methyl}amino)propyl] phosphonic acid;
2-({[5-(4-hexylphenyl)quinolin-8-yl]methyl}amino)ethyl dihydrogen phosphate;
3-({[5-(4-hexylphenyl)quinolin-8-yl]methyl}amino)propanoic acid;
{3-[({5-[4-(3-phenylpropyl)phenyl]quinolin-8-yl}methyl) amino]propyl}phosphonic acid;
(3-{[(5-{4-[3-(2-methylphenyl)propyl]phenyl}quinolin-8-yl)methyl]amino}propyl)phosphonic acid;
[3-({[5-(4-hexylphenyl)quinolin-8-yl]methyl}amino)butyl] phosphonic acid;
{3-[({5-[3-fluoro-4-(3-phenylpropyl)phenyl]quinolin-8-yl}methyl)amino]propyl}phosphonic acid;
[3-({[5-(2-fluoro-4-heptylphenyl)quinolin-8-yl] methyl}amino)propyl]phosphonic acid;
[3-({[5-(3-fluoro-4-heptylphenyl)quinolin-8-yl] methyl}amino)propyl]phosphonic acid;
{3-[({5-[4-(3-ethylheptyl)phenyl]quinolin-8-yl}methyl) amino]propyl}phosphonic acid;
[3-({[5-(4-octylphenyl)quinolin-8-yl]methyl}amino)propyl] phosphonic acid;

[3-({[5-(3-fluoro-4-hexylphenyl)quinolin-8-yl]methyl}amino)propyl]phosphonic acid;

{3-[({5-[4-(2-cyclohexylethyl)phenyl]quinolin-8-yl}methyl)amino]propyl}phosphonic acid;

2-({[5-(4-hexylphenyl)quinolin-8-yl]methyl}amino)ethanol;

(3-{[(5-{3-fluoro-4-[3-(2-methylphenyl)propyl]phenyl}quinolin-8-yl)methyl]amino}propyl)phosphonic acid;

(3-{[(5-{3-fluoro-4-[3-(3-methylphenyl)propyl]phenyl}quinolin-8-yl)methyl]amino}propyl)phosphonic acid;

(3-{[(5-{3-fluoro-4-[3-(4-methylphenyl)propyl]phenyl}quinolin-8-yl)methyl]amino}propyl)phosphonic acid;

{3-[({5-[4-(3-ethylheptyl)-3-fluorophenyl]quinolin-8-yl}methyl)amino]propyl}phosphonic acid;

{3-[({5-[4-(2-cyclohexylethyl)-3-fluorophenyl]quinolin-8-yl}methyl)amino]propyl}phosphonic acid;

2-[({5-[4-(3-ethylheptyl)-3-fluorophenyl]quinolin-8-yl}methyl)amino]ethanol;

2-[({5-[4-(3-ethylheptyl)-3-fluorophenyl]quinolin-8-yl}methyl)amino]ethyl dihydrogen phosphate.

Some compounds of Formula I and some of their intermediates have at least one stereogenic center in their structure. This stereogenic center may be present in an R or S configuration, said R and S notation is used in correspondence with the rules described in Pure Appli. Chem. (1976), 45, 11-13.

The term "pharmaceutically acceptable salts" refers to salts or complexes that retain the desired biological activity of the above identified compounds and exhibit minimal or no undesired toxicological effects. The "pharmaceutically acceptable salts" according to the invention include therapeutically active, non-toxic base or acid salt forms, which the compounds of Formula I are able to form.

The acid addition salt form of a compound of Formula I that occurs in its free form as a base can be obtained by treating the free base with an appropriate acid such as an inorganic acid, such as for example, hydrochloric acid, hydrobromic acid, sulfuric acid, phosphoric acid, nitric acid and the like; or an organic acid such as for example, acetic, hydroxyacetic, propanoic, lactic, pyruvic, malonic, fumaric acid, maleic acid, oxalic acid, tartaric acid, succinic acid, malic acid, ascorbic acid, benzoic acid, tannic acid, pamoic acid, citric, methylsulfonic, ethanesulfonic, benzenesulfonic, formic and the like (Handbook of Pharmaceutical Salts, P. Heinrich Stahal & Camille G. Wermuth (Eds), Verlag Helvetica Chemica Acta-Zurich, 2002, 329-345).

The base addition salt form of a compound of Formula I that occurs in its acid form can be obtained by treating the acid with an appropriate base such as an inorganic base, for example, sodium hydroxide, magnesium hydroxide, potassium hydroxide, calcium hydroxide, ammonia and the like; or an organic base such as for example, L-Arginine, ethanolamine, betaine, benzathine, morpholine and the like. (Handbook of Pharmaceutical Salts, P. Heinrich Stahal & Camille G. Wermuth (Eds), Verlag Helvetica Chemica Acta-Zurich, 2002, 329-345).

Compounds of Formula I and their salts can be in the form of a solvate, which is included within the scope of the present invention. Such solvates include for example hydrates, alcoholates and the like.

With respect to the present invention reference to a compound or compounds, is intended to encompass that compound in each of its possible isomeric forms and mixtures thereof unless the particular isomeric form is referred to specifically.

Compounds according to the present invention may exist in different polymorphic forms. Although not explicitly indicated in the above formula, such forms are intended to be included within the scope of the present invention.

The compounds of the invention are indicated for use in treating or preventing conditions in which there is likely to be a component involving the sphingosine-1-phosphate receptors.

In another embodiment, there are provided pharmaceutical compositions including at least one compound of the invention in a pharmaceutically acceptable carrier.

In a further embodiment of the invention, there are provided methods for treating disorders associated with modulation of sphingosine-1-phosphate receptors. Such methods can be performed, for example, by administering to a subject in need thereof a pharmaceutical composition containing a therapeutically effective amount of at least one compound of the invention.

These compounds are useful for the treatment of mammals, including humans, with a range of conditions and diseases that are alleviated by S1P modulation: not limited to the treatment of diabetic retinopathy, other retinal degenerative conditions, dry eye, angiogenesis and wounds.

Therapeutic utilities of S1P modulators are ocular diseases, such as but not limited to: wet and dry age-related macular degeneration, diabetic retinopathy, retinopathy of prematurity, retinal edema, geographic atrophy, angiogenesis inhibition, glaucomatous optic neuropathy, chorioretinopathy, hypertensive retinopathy, ocular ischemic syndrome, prevention of inflammation-induced fibrosis in the back of the eye, various ocular inflammatory diseases including uveitis, scleritis, keratitis, and retinal vasculitis; or systemic vascular barrier related diseases such as but not limited to: various inflammatory diseases, including acute lung injury, its prevention, sepsis, tumor metastasis, atherosclerosis, pulmonary edemas, and ventilation-induced lung injury; or autoimmune diseases and immunosuppression such as but not limited to: rheumatoid arthritis, Crohn's disease, Graves' disease, inflammatory bowel disease, multiple sclerosis, Myasthenia gravis, Psoriasis, ulcerative colitis, antoimmune uveitis, renal ischemia/perfusion injury, contact hypersensitivity, atopic dermitatis, and organ transplantation; or allergies and other inflammatory diseases such as but not limited to: urticaria, bronchial asthma, and other airway inflammations including pulmonary emphysema and chronic obstructive pulmonary diseases; or cardiac protection such as but not limited to: ischemia reperfusion injury and atherosclerosis; or wound healing such as but not limited to: scar-free healing of wounds from cosmetic skin surgery, ocular surgery, GI surgery, general surgery, oral injuries, various mechanical, heat and burn injuries, prevention and treatment of photoaging and skin ageing, and prevention of radiation-induced injuries; or bone formation such as but not limited to: treatment of osteoporosis and various bone fractures including hip and ankles; or antinociceptive activity such as but not limited to: visceral pain, pain associated with diabetic neuropathy, rheumatoid arthritis, chronic knee and joint pain, tendonitis, osteoarthritis, neuropathic pains; or central nervous system neuronal activity in Alzheimer's disease, age-related neuronal injuries; or in organ transplant such as renal, corneal, cardiac or adipose tissue transplant.

In still another embodiment of the invention, there are provided methods for treating disorders associated with modulation of sphingosine-1-phosphate receptors. Such methods can be performed, for example, by administering to a subject in need thereof a therapeutically effective amount of at least one compound of the invention, or any combination thereof, or pharmaceutically acceptable salts, hydrates, solvates, crystal forms and individual isomers, enantiomers, and diastereomers thereof.

The present invention concerns the use of a compound of Formula I or a pharmaceutically acceptable salt thereof, for the manufacture of a medicament for the treatment of ocular disease, wet and dry age-related macular degeneration, diabetic retinopathy, retinopathy of prematurity, retinal edema, geographic atrophy, glaucomatous optic neuropathy, chorioretinopathy, hypertensive retinopathy, ocular ischemic syndrome, prevention of inflammation-induced fibrosis in the back of the eye, various ocular inflammatory diseases including uveitis, scleritis, keratitis, and retinal vasculitis; or systemic vascular barrier related diseases, various inflammatory diseases, including acute lung injury, its prevention, sepsis, tumor metastasis, atherosclerosis, pulmonary edemas, and ventilation-induced lung injury; or autoimmune diseases and immunosuppression, rheumatoid arthritis, Crohn's disease, Graves' disease, inflammatory bowel disease, multiple sclerosis, Myasthenia gravis, Psoriasis, ulcerative colitis, antoimmune uveitis, renal ischemia/perfusion injury, contact hypersensitivity, atopic dermitis, and organ transplantation; or allergies and other inflammatory diseases, urticaria, bronchial asthma, and other airway inflammations including pulmonary emphysema and chronic obstructive pulmonary diseases; or cardiac protection, ischemia reperfusion injury and atherosclerosis; or wound healing, scar-free healing of wounds from cosmetic skin surgery, ocular surgery, GI surgery, general surgery, oral injuries, various mechanical, heat and burn injuries, prevention and treatment of photoaging and skin ageing, and prevention of radiation-induced injuries; or bone formation, treatment of osteoporosis and various bone fractures including hip and ankles; or anti-nociceptive activity, visceral pain, pain associated with diabetic neuropathy, rheumatoid arthritis, chronic knee and joint pain, tendonitis, osteoarthritis, neuropathic pains; or central nervous system neuronal activity in Alzheimer's disease, age-related neuronal injuries; or in organ transplant such as renal, corneal, cardiac or adipose tissue transplant.

The actual amount of the compound to be administered in any given case will be determined by a physician taking into account the relevant circumstances, such as the severity of the condition, the age and weight of the patient, the patient's general physical condition, the cause of the condition, and the route of administration.

The patient will be administered the compound orally in any acceptable form, such as a tablet, liquid, capsule, powder and the like, or other routes may be desirable or necessary, particularly if the patient suffers from nausea. Such other routes may include, without exception, transdermal, parenteral, subcutaneous, intranasal, via an implant stent, intrathecal, intravitreal, topical to the eye, back to the eye, intramuscular, intravenous, and intrarectal modes of delivery. Additionally, the formulations may be designed to delay release of the active compound over a given period of time, or to carefully control the amount of drug released at a given time during the course of therapy.

In another embodiment of the invention, there are provided pharmaceutical compositions including at least one compound of the invention in a pharmaceutically acceptable carrier thereof. The phrase "pharmaceutically acceptable" means the carrier, diluent or excipient must be compatible with the other ingredients of the formulation and not deleterious to the recipient thereof.

Pharmaceutical compositions of the present invention can be used in the form of a solid, a solution, an emulsion, a dispersion, a patch, a micelle, a liposome, and the like, wherein the resulting composition contains one or more compounds of the present invention, as an active ingredient, in admixture with an organic or inorganic carrier or excipient suitable for enteral or parenteral applications. Invention compounds may be combined, for example, with the usual non-toxic, pharmaceutically acceptable carriers for tablets, pellets, capsules, suppositories, solutions, emulsions, suspensions, and any other form suitable for use. The carriers which can be used include glucose, lactose, gum acacia, gelatin, mannitol, starch paste, magnesium trisilicate, talc, corn starch, keratin, colloidal silica, potato starch, urea, medium chain length triglycerides, dextrans, and other carriers suitable for use in manufacturing preparations, in solid, semisolid, or liquid form. In addition auxiliary, stabilizing, thickening and coloring agents and perfumes may be used. Invention compounds are included in the pharmaceutical composition in an amount sufficient to produce the desired effect upon the process or disease condition.

Pharmaceutical compositions containing invention compounds may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known in the art for the manufacture of pharmaceutical compositions and such compositions may contain one or more agents selected from the group consisting of a sweetening agent such as sucrose, lactose, or saccharin, flavoring agents such as peppermint, oil of wintergreen or cherry, coloring agents and preserving agents in order to provide pharmaceutically elegant and palatable preparations. Tablets containing invention compounds in admixture with non-toxic pharmaceutically acceptable excipients may also be manufactured by known methods. The excipients used may be, for example, (1) inert diluents such as calcium carbonate, lactose, calcium phosphate or sodium phosphate; (2) granulating and disintegrating agents such as corn starch, potato starch or alginic acid; (3) binding agents such as gum tragacanth, corn starch, gelatin or acacia, and (4) lubricating agents such as magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

In some cases, formulations for oral use may be in the form of hard gelatin capsules wherein the invention compounds are mixed with an inert solid diluent, for example, calcium carbonate, calcium phosphate or kaolin. They may also be in the form of soft gelatin capsules wherein the invention compounds are mixed with water or an oil medium, for example, peanut oil, liquid paraffin or olive oil.

The pharmaceutical compositions may be in the form of a sterile injectable suspension. This suspension may be formulated according to known methods using suitable dispersing or wetting agents and suspending agents. The sterile injectable preparation may also be a sterile injectable solution or suspension in a non-toxic parenterally-acceptable diluent or solvent, for example, as a solution in 1,3-butanediol. Sterile, fixed oils are conventionally employed as a solvent or suspending medium. For this purpose any bland fixed oil may be employed including synthetic mono- or diglycerides, fatty acids (including oleic acid), naturally occurring vegetable oils like sesame oil, coconut oil, peanut oil, cottonseed oil, etc., or synthetic fatty vehicles like ethyl oleate or the like. Buffers, preservatives, antioxidants, and the like can be incorporated as required.

Invention compounds may also be administered in the form of suppositories for rectal administration of the drug. These compositions may be prepared by mixing the invention compounds with a suitable non-irritating excipient, such as cocoa butter, synthetic glyceride esters of polyethylene glycols, which are solid at ordinary temperatures, but liquefy and/or dissolve in the rectal cavity to release the drug.

Since individual subjects may present a wide variation in severity of symptoms and each drug has its unique therapeutic characteristics, the precise mode of administration and dosage employed for each subject is left to the discretion of the practitioner.

The compounds and pharmaceutical compositions described herein are useful as medicaments in mammals, including humans, for treatment of diseases and/or alleviations of conditions which are responsive to treatment by agonists or functional antagonists of sphingosine-1-phosphate receptors. Thus, in further embodiments of the invention, there are provided methods for treating a disorder associated with modulation of sphingosine-1-phosphate receptors. Such methods can be performed, for example, by administering to a subject in need thereof a pharmaceutical composition containing a therapeutically effective amount of at least one invention compound. As used herein, the term "therapeutically effective amount" means the amount of the pharmaceutical composition that will elicit the biological or medical response of a subject in need thereof that is being sought by the researcher, veterinarian, medical doctor or other clinician. In some embodiments, the subject in need thereof is a mammal. In some embodiments, the mammal is human.

The present invention concerns also processes for preparing the compounds of Formula I. The compounds of formula I according to the invention can be prepared analogously to conventional methods as understood by the person skilled in the art of synthetic organic chemistry. The synthetic schemes set forth below, illustrate how compounds according to the invention can be made.

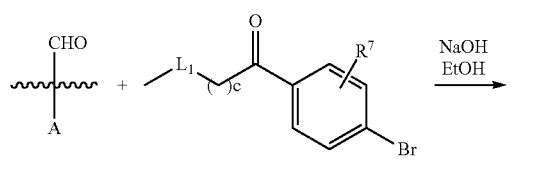

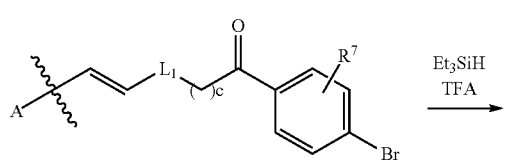

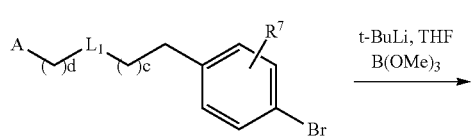

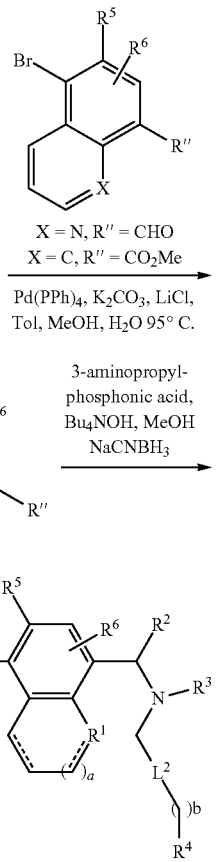

To a solution of appropriately substituted bromophenone in ethanol is added sodium hydroxide followed by a solution of aldehyde. The reaction mixture is stirred at room temperature and then an extraction with water and ethyl acetate is performed. The ene-one formed is reduced in the presence of trifluorocaetic acid and triethylsilane to afford the corresponding saturated arylbromide. This arylbromide will be reacted with the desired bromoquinolone aldehyde or bromo naphthylmethylester after treated with t-butyllithium and trimethylborate. The compound of Formula I is obtained from the reaction between the quinolone aldehyde or the naphthylmethyester and the phosphoric derivative.

Those skilled in the art will be able to routinely modify and/or adapt the following scheme to synthesize any compounds of the invention covered by Formula I.

DETAILED DESCRIPTION OF THE INVENTION

Figure 1:
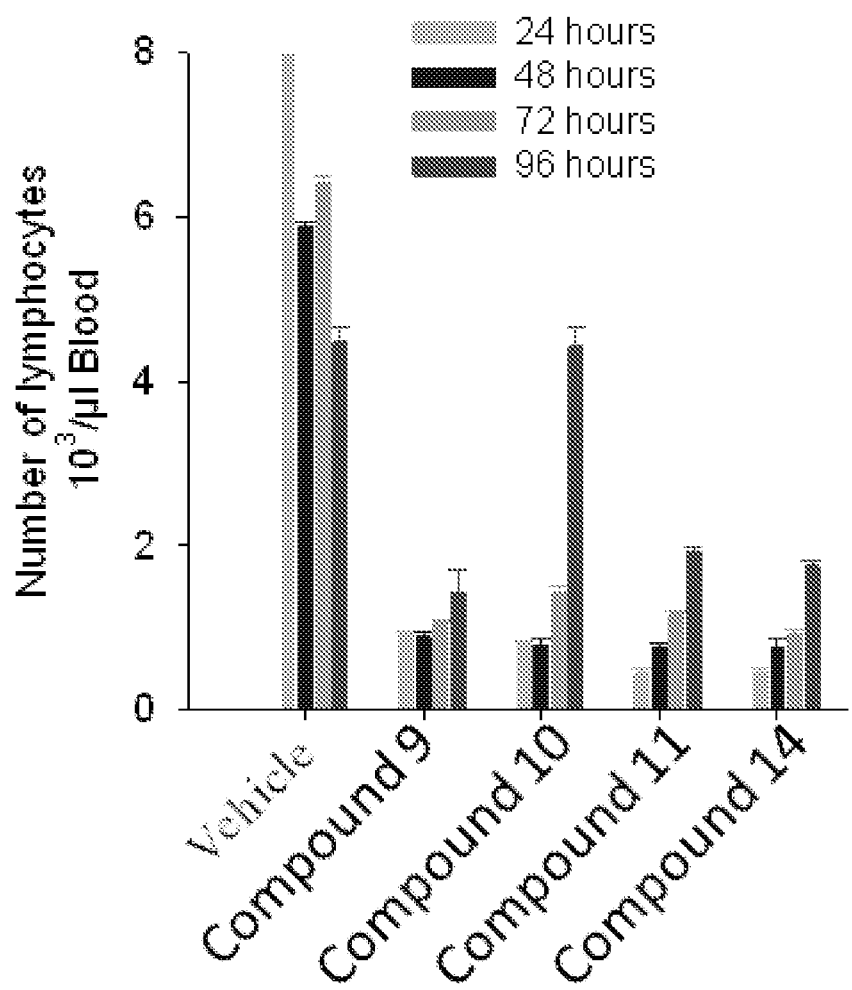
FIG. 1 shows that Compounds 9, 10, 11 and 14 lowered lymphocyte count after 24 hours in a lymphopenia assay in mice, by measuring the in vivo blood lymphocyte depletion after dosing.

It is to be understood that both the foregoing general description and the following detailed description are exemplary and explanatory only and are not restrictive of the invention claimed. As used herein, the use of the singular includes the plural unless specifically stated otherwise.

It will be readily apparent to those skilled in the art that some of the compounds of the invention may contain one or more asymmetric centers, such that the compounds may exist in enantiomeric as well as in diastereomeric forms. Unless it is specifically noted otherwise, the scope of the present invention includes all enantiomers, diastereomers and racemic mixtures. Some of the compounds of the invention may form salts with pharmaceutically acceptable acids or bases, and such pharmaceutically acceptable salts of the compounds described herein are also within the scope of the invention.

The present invention includes all pharmaceutically acceptable isotopically enriched compounds. Any compound of the invention may contain one or more isotopic atoms enriched or different than the natural ratio such as deuterium $^2$H (or D) in place of protium $^1$H (or H) or use of $^{13}$C enriched material in place of $^{12}$C and the like. Similar substitutions can be employed for N, O and S. The use of isotopes may assist in analytical as well as therapeutic aspects of the invention. For example, use of deuterium may increase the in vivo half-life by altering the metabolism (rate) of the compounds of the invention. These compounds can be prepared in accord with the preparations described by use of isotopically enriched reagents.

The following examples are for illustrative purposes only and are not intended, nor should they be construed as limiting the invention in any manner. Those skilled in the art will appreciate that variations and modifications of the following examples can be made without exceeding the spirit or scope of the invention.

As will be evident to those skilled in the art, individual isomeric forms can be obtained by separation of mixtures thereof in conventional manner. For example, in the case of diasteroisomeric isomers, chromatographic separation may be employed.

Compound names were generated with ACD version 8; and Intermediates and reagent names used in the examples were generated with software such as Chem Bio Draw Ultra version 12.0 or Auto Nom 2000 from MDL ISIS Draw 2.5 SP1.

In general, characterization of the compounds is performed according to the following methods:

NMR spectra are recorded on 300 and/or 600 MHz Varian and acquired at room temperature. Chemical shifts are given in ppm referenced either to internal TMS or to the solvent signal.

All the reagents, solvents, catalysts for which the synthesis is not described are purchased from chemical vendors such as Sigma Aldrich, Fluka, Bio-Blocks, Combi-blocks, TCI, VWR, Lancaster, Oakwood, Trans World Chemical, Alfa, Fisher, Maybridge, Frontier, Matrix, Ukrorgsynth, Toronto, Ryan Scientific, SiliCycle, Anaspec, Syn Chem, AK Scientific, AM FineCom, Carbocore, Chem-Impex, MIC-scientific, Ltd; however some known intermediates, were prepared according to published procedures.

Usually the compounds of the invention were purified by column chromatography (Auto-column) on an Teledyne-ISCO CombiFlash with a silica column, unless noted otherwise.

The following abbreviations are used in the examples:

| | |
|---|---|
| DMF | N,N-dimethylformamide |
| CDCl$_3$ | deuterated chloroform |
| CD$_3$OD | deuterated methanol |
| MPLC | medium pressure liquid chromatography |
| THF | tetrahydrofuran |
| MeOH | methanol |
| AcOH | acetic acid |
| RT | room temperature |
| NaOH | sodium hydroxide |
| MgSO$_4$ | magnesium sulfate |
| TFA | trifluoroacetic acid |
| DIBAL | diisobutylaluminium hydride |
| NMO | N-methylmorpholine-N-oxide |
| LiCl | lithium chloride |
| HCl | hydrochloric acid |

Those skilled in the art will be able to routinely modify and/or adapt the following schemes to synthesize any compound of the invention covered by Formula I.

Some compounds of this invention can generally be prepared in one step from commercially available literature starting materials.

Example 1

Intermediate 1

(2E)-1-(4-bromo-2-fluorophenyl)-3-phenylprop-2-en-1-one

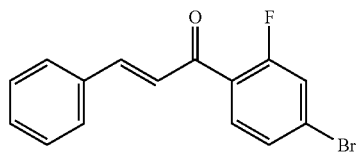 [SMILES: O=C(/C=C/c1ccccc1)c1ccc(Br)cc1F]

To a solution of 4-bromo-2-fluoroacetophenone (CAS 625446-22-2) (2.5 g, 11.5 mmol) in ethanol (20 mL) were added to a NaOH solution (576 mg in 4.4 mL water) followed by a solution of benzaldehyde (1.22 g) in ethanol (7 mL) with stirring. After stirring for 16 h at RT, the reaction mixture was diluted with water and extracted with ethyl acetate. The combined organic layers were washed with brine, dried over MgSO$_4$, and concentrated under reduced pressure. Purification by MPLC (5% ethyl acetate in hexanes) gave 737 mg of the Intermediate 1 as colorless solid.

$^1$H NMR (600 MHz, CDCl$_3$) δ 7.75 (dd, J=1.76, 15.85 Hz, 1H), 7.72 (t, J=8.07 Hz, 1H), 7.61-7.63 (m, 2H), 7.41-7.43 (m, 4H), 7.34-7.38 (m, 2H).

Intermediates 2-4 were prepared from the corresponding bromo-acetophenone and aldehyde, in a similar manner to the procedure described in Example 1 for Intermediate 1. The results are tabulated below in Table 1.

TABLE 1

| Interm No. | IUPAC name Structure | $^1$H NMR δ (ppm) |
|---|---|---|
| 2 | (2E)-3-(4-bromo-2-fluorophenyl)-1-(2-methylphenyl)prop-2-en-1-one | $^1$H NMR (600 MHz, CDCl$_3$) δ: 7.55 (d, J = 16.1 Hz, 1H), 7.52 (d, J = 8.2 Hz, 1H), 7.46 (dd, J = 8.1 Hz, 1H), 7.40 (dd, J = 7.9 Hz, 1H), 7.27-7.35 (m, 4H), 7.24 (d, J = 16.7 Hz, 1H), 2.46 (s, 3H) |
| 3 | (2E)-3-(4-bromo-2-fluorophenyl)-1-(3-methylphenyl)prop-2-en-1-one | $^1$H NMR (600 MHz, CDCl$_3$) δ: 7.80-7.83 (m, 3H), 7.63 (d, J = 15.8 Hz, 1H), 7.52 (t, J = 8.2 Hz, 1H), 7.38-7.42 (m, 2H), 7.33-7.36 (m, 2H), 2.45 (s, 3H) |
| 4 | (2E)-3-(4-bromo-2-fluorophenyl)-1-(4-methylphenyl)prop-2-en-1-one | $^1$H NMR (600 MHz, CDCl$_3$) δ: 7.93 (d, J = 8.2 Hz, 2H), 7.81 (d, J = 15.8 Hz, 1H), 7.63 (d, J = 15.8 Hz, 1H), 7.51 (dd, J = 8.5 Hz, 1H), 7.32-7.36 (m, 2H), 7.31 (d, J = 7.9 Hz, 2H), 2.44 (s, 3H) |

Example 2

Intermediate 5

1-(4-bromophenyl)-2-cyclohexylethanol

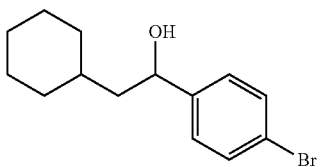 [SMILES: OC(CC1CCCCC1)c1ccc(Br)cc1]

To a solution of 4-bromo benzaldehyde (2.34 g, 12.64 mmol) in diethyl ether (20 mL) at −25° C. was added cyclohexylmethylmagnesium bromide (25.3 mL, 12.64 mmol). After stirring at 0° C. for 1 h, the reaction mixture was queneched with a saturated aqueous solution of ammonium chloride and extracted with ether. The combined ethereal layers were washed with brine, dried over MgSO$_4$, and concentrated under reduced pressure. Purification by MPLC (10% ethyl acetate in hexanes) gave (1.75 g, 49%) Intermediate as colorless oil.

$^1$H NMR (600 MHz, CDCl$_3$) δ: 7.46 (d, J=8.2 Hz, 2H), 7.22 (d, J=8.5 Hz, 2H), 4.76 (dd, J=8.7, 5.1 Hz, 1H), 1.77-1.81 (m, 1H), 1.63-1.74 (m, 6H), 1.46-1.51 (m, 1H), 1.35-1.43 (m, 1H), 1.14-1.26 (m, 2H), 0.95 (quindd, J=12.4, 12.0, 2.9 Hz, 2H).

Intermediates 6-10 were prepared from the corresponding aldehyde and the magnesium bromide, in a similar manner to the procedure described in Example 2 for Intermediate 5. The results are tabulated below in Table 2.

TABLE 2

| Interm No. | IUPAC name Structure | $^1$H NMR δ (ppm) |
|---|---|---|
| 6 | 1-(4-bromo-2-fluorophenyl)heptan-1-ol | $^1$H NMR (600 MHz, CDCl$_3$) δ: 7.50 (dd, J = 8.2, 7.0 Hz, 1H), 7.14 (dd, J = 9.5, 1.9 Hz, 1H), 7.00 (dd, J = 8.2, 1.8 Hz, 1H), 4.65 (dd, J = 7.3, 5.9 Hz, 1H), 1.80 (br. s., 1H), 1.64-1.78 (m, 3H), 1.34-1.42 (m, 1H), 1.23-1.33 (m, 8H), 0.87 (t, J = 7.0 Hz, 3H) |

TABLE 2-continued

| Interm No. | IUPAC name Structure | $^1$H NMR δ (ppm) |
|---|---|---|
| 7 | 1-(4-bromophenyl)-3-ethylheptan-1-ol | $^1$H NMR (600 MHz, CDCl$_3$) δ 7.47 (d, J = 8.22 Hz, 2H), 7.23 (d, J = 8.22 Hz, 2H), 4.72 (dd, J = 5.28, 8.51 Hz, 1H), 1.71 (dddd, J = 5.43, 8.51, 10.27, 13.94 Hz, 2H), 1.50-1.57 (m, 1H), 1.20-1.42 (m, 8H), 0.82-0.90 (m, 6H) |
| 8 | 1-(4-bromo-2-fluorophenyl)-3-ethylheptan-1-ol | |
| 9 | 1-(4-bromo-2-fluorophenyl)-2-cyclohexylethanol | $^1$H NMR (300 MHz, CDCl$_3$) δ 7.18-7.46 (m, 3H), 5.08 (dd, J = 4.98, 8.79 Hz, 1H), 1.60-1.81 (m, 5H), 1.39-1.59 (m, 2H), 1.13-1.35 (m, 4H), 0.85-1.04 (m, 2H) |
| 10 | 1-(4-bromo-2-fluorophenyl)hexan-1-ol | $^1$H NMR (600 MHz, CDCl$_3$) δ 7.35 (t, J = 8.20 Hz, 1H), 7.29 (dd, J = 1.47, 8.22 Hz, 1H), 7.20 (dd, J = 1.76, 9.68 Hz, 1H), 4.96 (dd, J = 5.72, 7.48 Hz, 1H), 1.67-1.81 (m, 3H), 1.39-1.46 (m, 1H), 1.26-1.33 (m, 4H), 0.88 (t, J = 6.50 Hz, 3H) |

Example 3

Intermediate 11

1-[3-(4-bromophenyl)propyl]-2-methylbenzene

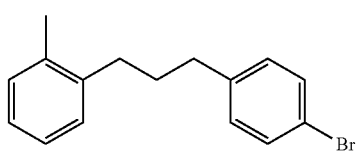 [SMILES: Cc1ccccc1CCCc1ccc(Br)cc1]

To a solution of (2E)-1-(4-bromophenyl)-3-(2-methylphenyl)prop-2-en-1-one (CAS 264229-42-7) (3.85 g, 12.8 mmol) in TFA (70 mL) at 0° C. was added triethylsilane (10.2 mL, 63.9 mmol) dropwise. After stirring at RT for 16 h, the reaction mixture was concentrated under reduced pressure. Purification by MPLC (hexanes) gave 2.7 g of Intermediate 11 as colorless oil.

$^1$H NMR (600 MHz, CDCl$_3$) δ: 7.34-7.36 (m, 2H), 7.06-7.11 (m, 4H), 7.00-7.02 (m, 2H), 2.59 (q, J=8.80 Hz, 4H), 2.23 (s, 3H), 1.81-1.87 (m, 2H).

Intermediates 12-22 were prepared from the corresponding ene-ones, TFA and triethylsilane, in a similar manner to the procedure described in Example 3 for Intermediate 11. The results are tabulated below in Table 3.

TABLE 3

| Interm. No. | IUPAC name Structure | Starting material | ¹H NMR δ (ppm) |
|---|---|---|---|
| 12 | 4-bromo-2-fluoro-1-(3-phenylpropyl)benzene | Intermediate 1 | ¹H NMR (600 MHz, CDCl₃) δ 7.28 (td, J = 1.80, 7.63 Hz, 2H), 7.17-7.20 (m, 5H), 7.03-7.06 (m, 1H), 2.64 (dt, J = 7.78, 11.74 Hz, 4H), 1.89-1.95 (m, 2H) |
| 13 | 4-bromo-2-fluoro-1-[3-(3-methylphenyl)propyl]benzene | Intermediate 2 | ¹H NMR (600 MHz, CDCl₃) δ 7.17-7.21 (m, 2H), 7.05-7.14 (m, 5H), 2.68 (t, J = 7.63 Hz, 2H), 2.63 (t, J = 7.90 Hz, 2H), 2.27 (s, 3H), 1.84-1.90 (m, 2H) |
| 14 | 4-bromo-1-(2-cyclohexylethyl)-2-fluorobenzene | Intermediate 9 | ¹H NMR (300 MHz, CDCl₃) δ 7.15-7.21 (m, 2H), 7.05 (dd, J = 7.62, 8.50 Hz, 1H), 2.56-2.62 (m, 2H), 1.60-1.80 (m, 5H), 1.41-1.50 (m, 2H), 1.11-1.31 (m, 4H), 0.89-0.99 (m, 2H) |
| 15 | 1-bromo-4-(2-cyclohexylethyl)benzene | Intermediate 5 | ¹H NMR (600 MHz, CDCl₃) δ 7.38 (d, J = 8.22 Hz, 2H), 7.04 (d, J = 8.22 Hz, 2H), 2.54-2.58 (m, 2H), 1.63-1.76 (m, 5H), 1.44-1.49 (m, 2H), 1.11-1.28 (m, 4H), 0.92 (dtd, J = 3.50, 11.20, 12.30 Hz, 2H) |
| 16 | 4-bromo-2-fluoro-1-[3-(3-methylphenyl)propyl]benzene | Intermediate 4 | ¹H NMR(600 MHz, CDCl₃) δ 7.17-7.20 (m, 2H), 7.02-7.10 (m, 5H), 2.61 (q, J = 7.34 Hz, 4H), 2.32 (s, 3H), 1.90 (quin, J = 7.78 Hz, 2H) |
| 17 | 4-bromo-2-fluoro-1-heptylbenzene | Intermediate 6 | ¹H NMR (300 MHz, CDCl₃) δ 7.18-7.21 (m, 1H), 7.15-7.18 (m, 1H), 7.04 (dd, J = 7.62, 8.50 Hz, 1H), 2.57 (t, J = 7.62 Hz, 2H), 1.57 (quin, J = 7.30 Hz, 2H), 1.24-1.34 (m, 8H), 0.88 (t, J = 6.90 Hz, 3H) |

TABLE 3-continued

| Interm. No. | IUPAC name Structure | Starting material | $^1$H NMR δ (ppm) |
|---|---|---|---|
| 18 | 1-bromo-4-(3-ethylheptyl)benzene | Intermediate 7 | $^1$H NMR (600 MHz, CDCl$_3$) δ 7.38 (d, J = 7.34 Hz, 2H), 7.05 (d, J = 8.22 Hz, 2H), 2.51-2.54 (m, 2H), 1.52 (ddd, J = 5.50, 5.72, 10.78 Hz, 2H), 1.23-1.36 (m, 9H), 0.90 (t, J = 7.04 Hz, 3H), 0.85 (t, J = 7.34 Hz, 3H) |
| 19 | 1-bromo-3-fluoro-4-(3-ethylheptyl)benzene | Intermediate 8 | $^1$H NMR (300 MHz, CDCl$_3$) δ 7.15-7.21 (m, 2H), 7.05 (t, J = 8.20 Hz, 1H), 2.52-2.58 (m, 2H), 1.47-1.55 (m, 2H), 1.18-1.39 (m, 8H), 0.89 (t, J = 7.00 Hz, 3H), 0.83 (s, 3H) |
| 20 | 4-bromo-2-fluoro-1-[3-(3-methylphenyl)propyl]benzene | Intermediate 3 | $^1$H NMR (600 MHz, CDCl$_3$) δ 7.16-7.20 (m, 3H), 7.05 (t, J = 8.07 Hz, 1H), 6.96-7.01 (m, 3H), 2.62 (dt, J = 8.10, 10.12 Hz, 4H), 2.32 (s, 3H), 1.88-1.93 (m, 2H) |
| 21 | 1-bromo-4-(3-phenylpropyl)benzene | 2-Propen-1-one, 1-(4-bromophenyl)-3-phenyl-, (2E)- (CAS 22966-23-0) | $^1$H NMR (600 MHz, CDCl$_3$) δ 7.39 (d, J = 8.22 Hz, 2H), 7.28 (t, J = 7.30 Hz, 2H), 7.16-7.20 (m, 3H), 7.05 (d, J = 8.51 Hz, 2H), 2.63 (t, J = 7.63 Hz, 2H), 2.60 (t, J = 7.63 Hz, 2H), 1.90-1.96 (m, 2H) |
| 22 | 4-bromo-2-fluoro-1-hexylbenzene | Intermediate 10 | $^1$H NMR (300 MHz, CDCl$_3$) δ 7.15-7.20 (m, 2H), 7.04 (t, J = 8.20 Hz, 1H), 2.58 (t, J = 7.76 Hz, 2H), 1.57 (quin, J = 7.90 Hz, 2H), 1.25-1.36 (m, 6H), 0.88 (t, J = 7.30 Hz, 3H) |

Example 4

Intermediate 23

5-[3-fluoro-4-(3-phenylpropyl)phenyl]quinoline-8-carbaldehyde

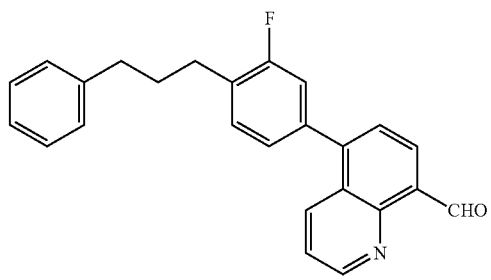 [SMILES: O=Cc1ccc(-c2ccc(CCCc3ccccc3)c(F)c2)c2cccnc12]

To a solution of Intermediate 12 (500 mg, 1.7 mmol) in THF (15 mL) at −78° C. was added t-butyllithium (1.7 M in pentane, 2.0 mL) slowly dropwise. After stirring at −78° C. for 1 h, trimethyl borate (0.39 mL, 3.46 mmol) was added. The reaction mixture was warmed at RT over 2 h. After stirring at RT for 15 min, the reaction mixture was quenched with saturated solution of ammonium chloride and extracted with ethyl acetate. The combined organic layers were washed with HCl (10% solution), brine, and dried (MgSO$_4$), filtered, and concentrated under reduced pressure to give 415 mg boronic acid as a colorless solid.

To a solution of the resulting boronic acid (4.07 mg, 1.5 mmol) and 5-bromoquinoline-8-carbaldehyde (CAS 885267-41-4) (292 mg, 1.4 mmol) in toluene (30 mL) were added potassium carbonate (436 mg, 3.15 mmol) and LiCl (67 mg) with stirring. After bubbling with Argon for 10 min, tetrakis(triphenylphosphine)palladium(0) (36 mg) was added and heated at 95° C. for 16 h. After the reaction mixture was cooled at RT, it was diluted with water and extracted with ethyl acetate. The combined organic layers were washed with brine, and dried (MgSO$_4$), filtered, and concentrated under reduced pressure. The residue was purified by MPLC (15% ethyl acetate in hexanes) gave 320 mg of Intermediate 23 as colorless solid.

$^1$H NMR (600 MHz, CDCl$_3$) δ 11.49 (s, 1H), 9.06 (dd, J=1.61, 3.96 Hz, 1H), 8.36 (d, J=7.63 Hz, 1H), 8.32 (dd, J=1.76, 8.51 Hz, 1H), 7.62 (d, J=7.34 Hz, 1H), 7.48 (dd, J=4.11, 8.51 Hz, 1H), 7.28-7.36 (m, 3H), 7.19-7.25 (m, 3H), 7.17 (dd, J=1.61, 7.78 Hz, 1H), 7.14 (dd, J=1.47, 10.27 Hz, 1H), 2.80 (t, J=7.63 Hz, 2H), 2.75 (t, J=7.60 Hz, 2H), 2.02-2.08 (m, 2H).

Intermediates 24-38 were prepared from the corresponding bromide in a similar manner to the procedure described in Example 4 for Intermediate 23. The results are tabulated below in Table 4.

TABLE 4

| Interm No. | IUPAC name Structure | Starting material | $^1$H NMR δ (ppm) |
|---|---|---|---|
| 24 | 5-[4-(3-phenylpropyl)phenyl]quinoline-8-carbaldehyde | Intermediate 21 | $^1$H NMR (600 MHz, CDCl$_3$) δ 11.50 (d, J = 0.59 Hz, 1H), 9.06 (dd, J = 1.76, 4.11 Hz, 1H), 8.37 (d, J = 7.34 Hz, 1H), 8.35 (d, J = 1.76 Hz, 1H), 7.64 (d, J = 7.34 Hz, 1H), 7.46 (dd, J = 4.11, 8.51 Hz, 1H), 7.35-7.40 (m, 4H), 7.29-7.33 (m, 2H), 7.20-7.24 (m, 3H), 2.77 (t, J = 7.60 Hz, 2H), 2.73 (t, J = 7.90 Hz, 2H), 2.03-2.09 (m, 2H) |
| 25 | 5-4-[3-(2-methylphenyl)propyl]phenylquinoline-8-carbaldehyde | Intermediate 11 | $^1$H NMR (600 MHz, CD$_3$OD) δ 8.98 (dd, J = 1.61, 4.26 Hz, 1H), 8.33 (dd, J = 1.47, 8.51 Hz, 1H), 7.92 (d, J = 7.34 Hz, 1H), 7.52-7.55 (m, 2H), 7.36-7.39 (m, 4H), 7.04-7.14 (m, 4H), 4.74 (s, 2H), 3.16 (t, J = 7.60 Hz, 2H), 2.79 (t, J = 8.20 Hz, 2H), 2.69 (t, J = 7.60 Hz, 2H), 2.27 (s, 3H), 2.00-2.07 (m, 2H), 1.92-1.98 (m, 2H), 1.63-1.73 (m, 2H) |

TABLE 4-continued

| Interm No. | IUPAC name Structure | Starting material | $^1$H NMR δ (ppm) |
|---|---|---|---|
| 26 | 5-(2-fluoro-4heptylphenyl)quinoline-8-carbaldehyde | 1-bromo-2-fluoro-4-hepylbenzene (CAS 256383-48-9) | $^1$H NMR (CDCl$_3$) δ 11.51 (d, J = 0.9 Hz, 1H), 9.06 (dd, J = 4.2, 1.9 Hz, 1H), 8.38 (d, J = 7.3 Hz, 1H), 8.12 (ddd, J = 8.5, 2.6, 1.8 Hz, 1H), 7.66 (d, J = 7.6 Hz, 1H), 7.48 (dd, J = 8.6, 4.2 Hz, 1H), 7.30 (d, J = 7.3 Hz, 1H), 7.13 (dd, J = 7.9, 1.8 Hz, 1H), 7.08 (dd, J = 10.8, 1.5 Hz, 1H), 2.69-2.74 (m, 2H), 1.70 (dt, J = 14.9, 7.5 Hz, 2H), 1.26-1.44 (m, 8H), 0.91 (t, J = 7.0 Hz, 3H) |
| 27 | 5-(3-fluoro-4heptylphenyl)quinoline-8-carbaldehyde | Intermediate 17 | $^1$H NMR (CDCl$_3$) δ 11.50 (s, 1H), 9.08 (dd, J = 4.1, 1.8 Hz, 1H), 8.38 (d, J = 7.3 Hz, 1H), 8.36 (dd, J = 8.5, 1.8 Hz, 1H), 7.65 (d, J = 7.3 Hz, 1H), 7.50 (dd, J = 8.8, 4.1 Hz, 1H), 7.35 (t, J = 7.8 Hz, 1H), 7.17 (dd, J = 7.6, 1.8 Hz, 1H), 7.14 (dd, J = 10.3, 1.8 Hz, 1H), 2.74 (t, J = 7.8 Hz, 2H), 1.70 (quin, J = 7.6 Hz, 2H), 1.29-1.44 (m, 8H), 0.91 (t, J = 7.0 Hz, 3H) |
| 28 | 5-(4-(3-ethylheptylphenyl)quinoline-8-carbaldehyde | Intermediate 18 | $^1$H NMR (CDCl$_3$) δ 11.49 (s, 1H), 9.04 (dd, J = 4.1, 1.8 Hz, 1H), 8.36 (dd, J = 8.5, 1.8 Hz, 1H), 8.36 (d, J = 7.3 Hz, 1H), 7.63 (d, J = 7.6 Hz, 1H), 7.45 (dd, J = 8.8, 4.1 Hz, 1H), 7.35-7.39 (m, 4H), 2.69 (dd, J = 10.1, 6.0 Hz, 2H), 1.63-1.67 (m, 2H), 1.28-1.43 (m, 9H), 0.92 (dt, J = 7.1 Hz, 6H) |
| 29 | 5-(4-octylphenyl)quinoline-8-carbaldehyde | 1-bromo-4-octylbenzene (CAS 51554-93-9) | $^1$H NMR (CDCl$_3$) δ 11.50 (s, 1H), 9.05 (dd, J = 3.7, 1.6 Hz, 1H), 8.36 (d, J = 7.3 Hz, 1H), 7.64 (d, J = 7.3 Hz, 1H), 7.46 (dd, J = 8.5, 4.1 Hz, 1H), 7.38 (d, J = 7.9 Hz, 2H), 7.35 (d, J = 7.9 Hz, 2H), 2.71 (t, J = 7.9 Hz, 2H), 1.70 (quin, J = 7.6 Hz, 2H), 1.25-1.43 (m, 10H), 0.90 (t, J = 6.7 Hz, 3H) |

TABLE 4-continued

| Interm No. | IUPAC name Structure | Starting material | ¹H NMR δ (ppm) |
|---|---|---|---|
| 30 | 5-(3-fluoro-4-(3-(m-tolyl)propyl)phenyl)quinoline-8-carbaldehyde | Intermediate 20 | ¹H NMR (CDCl₃) δ 11.50 (d, J = 0.9 Hz, 1H), 9.07 (dd, J = 4.1, 1.8 Hz, 1H), 8.38 (s, 1H), 8.34 (dd, J = 8.5, 1.8 Hz, 1H), 7.64 (dd, J = 7.5, 0.7 Hz, 1H), 7.49 (dd, J = 8.6, 4.2 Hz, 1H), 7.35 (t, J = 7.6 Hz, 1H), 7.12-7.22 (m, 3H), 6.96-7.06 (m, 3H), 2.80 (t, J = 7.8 Hz, 2H), 2.67-2.75 (m, 2H), 2.35 (s, 3H), 1.98-2.10 (m, 2H) |
| 31 | 5-(4-(2-cyclohexylethyl)phenyl)quinoline-8-carbaldehyde | Intermediate 15 | ¹H NMR (CDCl₃) δ 11.49 (d, J = 0.6 Hz, 1H), 9.04 (dd, J = 4.1, 1.8 Hz, 1H), 8.35 (d, J = 7.3 Hz, 1H), 8.36 (dd, J = 8.5, 2.3 Hz, 1H), 7.63 (d, J = 7.3 Hz, 1H), 7.45 (dd, J = 8.5, 4.1 Hz, 1H), 7.38 (d, J = 8.2 Hz, 2H), 7.34 (d, J = 7.9 Hz, 2H), 2.70-2.74 (m, 2H), 1.82 (dd, J = 13.5, 2.1 Hz, 2H), 1.73 (ddd, J = 12.8, 3.2, 2.8 Hz, 2H), 1.66-1.69 (m, 1H), 1.57-1.61 (m, 2H), 1.30-1.39 (m, 1H), 1.15-1.30 (m, 3H), 0.98 (dtd, J = 12.3, 12.1, 3.2 Hz, 2H) |
| 32 | 5-(4-(2-cyclohexylethyl)-3-fluorophenyl)quinoline-8-carbaldehyde | Intermediate 14 | ¹H NMR (CDCl₃) δ 11.49 (d, J = 0.6 Hz, 1H), 9.06 (dd, J = 4.1, 1.8 Hz, 1H), 8.36 (d, J = 7.6 Hz, 1H), 8.34 (dd, J = 8.5, 1.8 Hz, 1H), 7.63 (dd, J = 7.3, 0.6 Hz, 1H), 7.48 (dd, J = 8.5, 4.1 Hz, 1H), 7.34 (t, J = 7.9 Hz, 1H), 7.11-7.18 (m, 2H), 2.69-2.78 (m, 2H), 1.65-1.87 (m, 5H), 1.54-1.62 (m, 2H), 1.15-1.47 (m, 4H), 0.99 (dtd, J = 12.0, 11.6, 2.8 Hz, 2H) |
| 33 | 5-{3-fluoro-4-[3-(2-methylphenyl)propyl]phenyl}quinoline-8-carbaldehyde | Intermediate 13 | ¹H NMR (300 MHz, CDCl₃) δ 11.48 (d, J = 0.59 Hz, 1H), 9.04 (dd, J = 1.76, 4.10 Hz, 1H), 8.34 (d, J = 7.62 Hz, 1H), 8.31 (dd, J = 2.05, 8.79 Hz, 1H), 7.61 (dd, J = 0.59, 7.62 Hz, 1H), 7.46 (dd, J = 4.25, 8.64 Hz, 1H), 7.36 (t, J = 8.50 Hz, 1H), 7.11-7.20 (m, 7H), 2.78 (dt, J = 7.60, 33.11 Hz, 4H), 2.31 (s, 3H), 1.94-2.04 (m, 2H) |

TABLE 4-continued

| Interm No. | IUPAC name Structure | Starting material | $^1$H NMR δ (ppm) |
|---|---|---|---|
| 34 | 5-{3-fluoro-4-[3-(4-methylphenyl)propyl]phenyl}quinoline-8-carbaldehyde | Intermediate 16 | $^1$H NMR (300 MHz, CDCl$_3$) δ 11.50 (d, J = 0.88 Hz, 1H), 9.10 (dd, J = 1.76, 4.40 Hz, 1H), 8.39 (d, J = 7.62 Hz, 1H), 8.37 (dd, J = 1.76, 8.50 Hz, 1H), 7.65 (dd, J = 0.73, 7.47 Hz, 1H), 7.52 (dd, J = 4.25, 8.64 Hz, 1H), 7.35 (t, J = 7.90 Hz, 1H), 7.07-7.19 (m, 7H), 2.75 (dt, J = 7.90, 24.03 Hz, 4H), 2.33 (s, 3H), 1.99-2.07 (m, 2H) |
| 35 | methyl 4-(4hexylphenyl)-1-naphthoate | 1-bromo-4-hexylbenzene (CAS 237033-22-2) | $^1$H NMR (300 MHz, CDCl$_3$) δ 8.98 (ddt, J = 0.70, 0.88, 8.57 Hz, 1H), 8.20 (d, J = 7.62 Hz, 1H), 7.96 (ddd, J = 0.60, 1.47, 8.50 Hz, 1H), 7.61 (ddd, J = 1.47, 6.96, 8.57 Hz, 1H), 7.46 (ddd, J = 1.17, 6.89, 8.35 Hz, 1H), 7.43 (d, J = 7.33 Hz, 1H), 7.28-7.41 (m, 4H), 4.02 (s, 3H), 2.71 (t, J = 7.60 Hz, 2H), 1.65-1.75 (m, 2H), 1.26-1.44 (m, 6H), 0.91 (t, J = 7.00 Hz, 3H) |
| 36 | 5-(4-hexylphenyl)quinoline-8-carbaldehyde | 1-bromo-4-hexylbenzene (CAS 237033-22-2) | $^1$H NMR (300 MHz, CDCl$_3$) δ 11.50 (s, 1H), 9.06 (dd, J = 1.61, 3.96 Hz, 1H), 8.37 (d, J = 7.33 Hz, 2H), 7.65 (d, J = 7.33 Hz, 1H), 7.47 (dd, J = 4.25, 8.64 Hz, 1H), 7.33-7.40 (m, 4H), 2.72 (t, J = 7.60 Hz, 2H), 1.65-1.75 (m, 2H), 1.31-1.46 (m, 6H), 0.91 (t, J = 6.70 Hz, 3H) |
| 37 | 5-(3-fluoro-4-hexylphenyl)quinoline-8-carbaldehyde | Intermediate 22 | $^1$H NMR (300 MHz, CDCl$_3$) δ 11.49 (s, 1H), 9.05 (dd, J = 1.76, 4.10 Hz, 1H), 8.35 (d, J = 7.33 Hz, 1H), 8.34 (dd, J = 1.76, 8.79 Hz, 1H), 7.62 (d, J = 7.62 Hz, 1H), 7.48 (dd, J = 4.10, 8.79 Hz, 1H), 7.35 (t, J = 7.91 Hz, 1H), 7.15 (dd, J = 1.76, 19.05 Hz, 1H), 7.15 (s, 0H), 2.74 (t, J = 7.62 Hz, 2H), 1.64-1.74 (m, 2H), 1.30-1.47 (m, 6H), 0.91 (t, J = 6.70 Hz, 3H) |

TABLE 4-continued

| Interm No. | IUPAC name Structure | Starting material | $^1$H NMR δ (ppm) |
|---|---|---|---|
| 38 | 5-[4-(3-ethylheptyl)-3-fluorophenyl]quinoline-8-carbaldehyde<br><br>(structure) | Intermediate 19 | $^1$H NMR (300 MHz, CDCl$_3$) δ 11.51 (d, J = 0.88 Hz, 1H), 9.10 (dd, J = 1.90, 4.25 Hz, 1H), 8.39 (d, J = 7.62 Hz, 1H), 8.38 (dd, J = 1.76, 8.79 Hz. 1H), 7.65 (d, J = 7.33 Hz, 1H), 7.51 (dd, J = 4.25, 8.64 Hz, 1H), 7.36 (t, J = 7.90 Hz, 1H), 7.12-7.19 (m, 2H), 2.68-2.75 (m, 2H), 1.60-1.68 (m, 2H), 1.26-1.45 (m, 9H), 0.88-0.95 (m, 6H) |

Example 5

Intermediate 39

[4-(4-hexylphenyl)-1-naphthyl]methanol

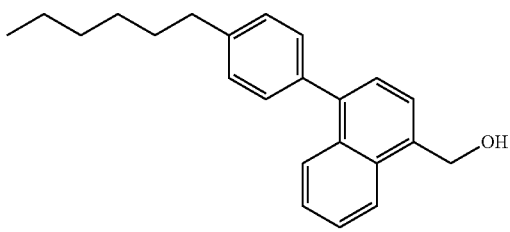 [SMILES: CCCCCCc1ccc(-c2ccc(CO)c3ccccc23)cc1]

To a solution of Intermediate 35 (297 mg, 1.1 mmol) in methylene chloride (10 mL) at −78° C. was added DIBAL (1M in methylene chloride, 2.8 mL, 2.8 mmol). After warming at RT over 3 h, the reaction mixture was cooled to −10° C. and quenched with ethyl acetate, methanol, and 10% HCl solution. The mixture was diluted with water and the aqueous layer was extracted with ethyl acetate. The combined organic layers were washed with brine, dried over MgSO$_4$, and concentrated under reduced pressure. Purification by MPLC (30% ethyl acetate in hexanes) gave 378 mg of Intermediate 39 as colorless oil.

$^1$H NMR (300 MHz, CDCl$_3$) δ 8.20 (dd, J=0.59, 8.50 Hz, 1H), 7.97 (dd, J=0.59, 8.50 Hz, 1H), 7.56 (ddd, J=1.50, 6.70, 8.21 Hz, 1H), 7.56 (d, J=8.50 Hz, 1H), 7.45 (ddd, J=1.47, 7.03, 8.79 Hz, 1H), 7.37-7.41 (m, 3H), 7.28-7.32 (m, 2H), 5.20 (s, 2H), 2.70 (t, J=7.60 Hz, 2H), 1.65-1.75 (m, 2H), 1.31-1.46 (m, 6H), 0.92 (t, J=6.70 Hz, 3H).

Example 6

Intermediate 40

4-(4-hexylphenyl)-1-naphthaldehyde

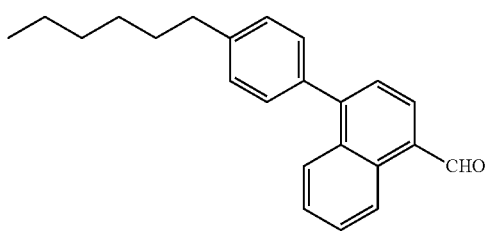 [SMILES: CCCCCCc1ccc(-c2ccc(C=O)c3ccccc23)cc1]

To a solution of Intermediate 39 (308 mg, 0.96 mmol), NMO (283 mg, 2.4 mmol), and 4 Å molecular sieves (0.4 g) in dichloromethane (10 mL) and acetonitrile (1.2 mL) was added tetrapropylammonium perruthenate (TPAP, 10 mg). After stirring at RT for 2 h, the reaction mixture was filtered through a short column of silica gel, eluted with ethyl acetate and concentrated under reduced pressure. Purification by MPLC (2% ethyl acetate in hexanes) gave rise to 242 mg of Intermediate 40 as colorless solid.

$^1$H NMR (300 MHz, CDCl$_3$) δ 10.42 (s, 1H), 9.36 (d, J=8.50 Hz, 1H), 8.02 (d, J=7.33 Hz, 1H), 8.00 (d, J=8.50 Hz, 1H), 7.70 (ddd, J=1.17, 7.03, 8.50 Hz, 1H), 7.57 (d, J=7.33 Hz, 1H), 7.53 (ddd, J=1.47, 7.30, 8.20 Hz, 1H), 7.31-7.42 (m, 4H), 2.72 (t, J=7.91 Hz, 2H), 1.65-1.76 (m, 2H), 1.31-1.46 (m, 6H), 0.92 (t, J=6.70 Hz, 3H).

Example 7

Intermediate 41

1-[5-(4-hexylphenyl)quinolin-8-yl]ethanone

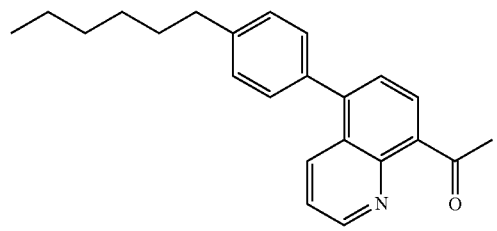 [SMILES: CCCCCCc1ccc(-c2ccc(C(C)=O)c3ncccc23)cc1]

To a solution of Intermediate 36 (166 mg, 0.52 mmol) in THF (3 mL) at −78° C. was added methyl lithium (1.6M in ether, 0.36 mL, 0.57 mmol) dropwise. After stirring at −78° C. for 20 min, a solution of N-t-butylbenzenesulfinimidoyl chloride (169 mg, 0.78 mmol) in THF (1.2 mL) was added dropwise. After stirring the reaction mixture for another 20 min at −78° C., then at RT for 20 min, the black solution mixture was quenched with 2M HCl (3 mL). The aqueous layer was extracted with ethyl acetate. The combined aqueous layers were then extracted well with ethyl acetate. The combined organic layers were washed with brine, dried over MgSO$_4$, and concentrated under reduced pressure. Purification by MPLC (20% ethyl acetate in hexanes) gave 25 mg of Intermediate 41 as brown oil.

¹H NMR (600 MHz, CDCl₃) δ 8.97 (dd, J=1.76, 4.11 Hz, 1H), 8.30 (dd, J=1.76, 8.51 Hz, 1H), 7.97 (d, J=7.63 Hz, 1H), 7.53 (d, J=7.34 Hz, 1H), 7.32-7.40 (m, 5H), 2.98 (s, 3H), 2.71 (t, J=8.20 Hz, 2H), 1.67-1.73 (m, 2H), 1.33-1.43 (m, 6H), 0.91 (t, J=7.00 Hz, 3H).

Example 8

Compound 1

[3-({[5-(4-hexylphenyl)quinolin-8-yl]methyl}amino)butyl]phosphonic acid

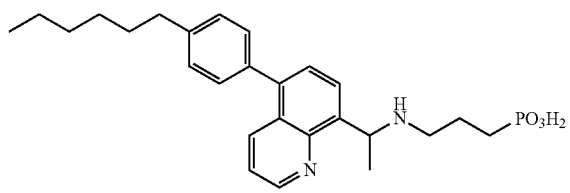

To a solution of Intermediate 41 (68 mg, 0.21 mmol) and (3-aminopropyl)phosphonic acid (29 mg, 0.21 mmol) in methanol (3 mL) was added tetrabutylammonium hydroxide (1M in MeOH, 0.21 mL, 0.21 mmol). The reaction mixture was heated at 50° C. for 2 h with stirring, then sodium cyanoborohydride (13 mg, 0.21 mmol) was added. The reaction mixture was heated at 50° C. with stirring for 3 h. After cooling to RT, the mixture was concentrated and purified by MPLC (0-100% ethyl acetate in hexanes) to give 26 mg of Compound 1 as yellow solid.

¹H NMR (600 MHz, CD₃OD) δ 8.96 (dd, J=1.76, 4.11 Hz, 1H), 8.36 (dd, J=1.76, 8.51 Hz, 1H), 7.86 (d, J=7.34 Hz, 1H), 7.57 (d, J=7.34 Hz, 1H), 7.55 (dd, J=4.10, 8.22 Hz, 1H), 7.37 (d, J=0.88 Hz, 4H), 5.03 (q, J=6.75 Hz, 1H), 2.90 (s, 1H), 2.79-2.84 (m, 1H), 2.72 (t, J=7.90 Hz, 2H), 1.88-1.95 (m, 2H), 1.85 (d, J=7.04 Hz, 3H), 1.61-1.73 (m, 4H), 1.34-1.45 (m, 6H), 0.92 (t, J=7.00 Hz, 3H).

Compounds 2 though 20 were prepared from the corresponding aldehyde or methylester in a similar manner to the procedure described in Example 8 for Compound 1 and in the general procedure described above. The results are tabulated below in Table 5.

TABLE 5

| Comp. No. | IUPAC name Structure | Starting material | ¹H NMR δ (ppm) |
|---|---|---|---|
| 2 | {3-[({5-[3-fluoro-4-(3-phenylpropyl)phenyl]quinolin-8-yl}methyl)amino]propyl}phosphonic acid | Intermediate 23 | ¹H NMR (600 MHz, CD₃OD) δ 9.00 (dd, J = 1.61, 4.25 Hz, 1H), 8.32 (dd, J = 1.61, 8.66 Hz, 1H), 7.94 (d, J = 7.34 Hz, 1H), 7.55-7.58 (m, 2H), 7.39 (t, J = 7.78 Hz, 1H), 7.13-7.28 (m, 7H), 4.75 (s, 2H), 3.18 (t, J = 6.60 Hz, 2H), 2.77 (t, J = 7.63 Hz, 2H), 2.71 (t, J = 7.63 Hz, 2H), 1.98-2.08 (m, 4H), 1.63-1.73 (m, 2H) |
| 3 | [3-({[4-(4-hexylphenyl)-1-naphthyl]methyl}amino)propyl]phosphonic acid | Intermediate 40 | ¹H NMR (600 MHz, CD₃OD) δ 8.22 (d, J = 8.51 Hz, 1H), 7.94 (d, J = 8.22 Hz, 1H), 7.73 (d, J = 7.34 Hz, 1H), 7.66 (ddd, J = 1.17, 6.90, 8.36 Hz, 1H), 7.52 (ddd, J = 1.17, 6.90, 8.36 Hz, 1H), 7.45 (d, J = 7.34 Hz, 1H), 7.34 (d, J = 1.17 Hz, 4H), 4.69 (s, 2H), 3.26 (t, J = 6.31 Hz, 2H), 2.72 (t, J = 8.50 Hz, 2H), 2.00-2.08 (m, J = 6.60, 6.75, 18.93 Hz, 2H), 1.68-1.75 (m, 4H), 1.35-1.44 (m, 6H), 0.92 (t, J = 7.30 Hz, 3H) |

TABLE 5-continued

| Comp. No. | IUPAC name Structure | Starting material | $^1$H NMR δ (ppm) |
|---|---|---|---|
| 4 | [3-({[5-(4-hexylphenyl)quinolin-8-yl]methyl}amino)propyl] phosphonic acid | Intermediate 36 | $^1$H NMR (300 MHz, CD$_3$OD) δ 8.98 (dd, J = 1.47, 4.10 Hz, 1H), 8.33 (dd, J = 1.47, 8.50 Hz, 1H), 7.93 (d, J = 7.33 Hz, 1H), 7.47-7.59 (m, 2H), 7.35 (s, 4H), 4.75 (s, 2H), 3.18 (t, J = 6.59 Hz, 2H), 2.71 (t, J = 7.62 Hz, 2H), 1.97-2.12 (m, 2H), 1.61-1.76 (m, 4H), 1.32-1.46 (m, 6H), 0.92 (t, J = 6.70 Hz, 3H) |
| 5 | 2-({[5-(4-hexylphenyl)quinolin-8-yl]methyl}amino)ethyl dihydrogen phosphate | Intermediate 36 | $^1$H NMR (600 MHz, CD$_3$OD) δ 8.99 (dd, J = 1.61, 4.26 Hz, 1H), 8.34 (dd, J = 1.61, 8.66 Hz, 1H), 7.94 (d, J = 7.34 Hz, 1H), 7.55 (d, J = 7.04 Hz, 1H), 7.54 (dd, J = 4.26, 8.66 Hz, 1H), 7.35-7.37 (m, 4H), 4.74 (s, 2H), 4.10 (tdd, J = 2.42, 2.79, 7.08 Hz, 2H), 2.72 (t, J = 7.60 Hz, 2H), 1.63-1.73 (m, 4H), 1.34-1.45 (m, 6H), 0.89-0.94 (m, J = 7.00, 7.00 Hz, 3H) |
| 6 | {3-[({5-[4-(3-phenylpropyl)phenyl]quinolin-8-yl}methyl)amino]propyl} phosphonic acid | Intermediate 24 | $^1$H NMR (600 MHz, CD$_3$OD) δ 8.98 (dd, J = 1.61, 4.26 Hz, 1H), 8.33 (dd, J = 1.76, 8.51 Hz, 1H), 7.92 (d, J = 7.34 Hz, 1H), 7.52-7.54 (m, 2H), 7.35 (s, 4H), 7.14-7.28 (m, 5H), 4.73 (s, 2H), 3.16 (t, J = 6.46 Hz, 2H), 2.73 (t, J = 7.30 Hz, 2H), 2.69 (t, J = 7.60 Hz, 2H), 1.98-2.07 (m, 4H), 1.63-1.73 (m, 2H) |
| 7 | 3-({[5-(4-hexylphenyl)quinolin-8-yl]methyl}amino)propanoic acid | Intermediate 36 | $^1$H NMR (600 MHz, CD$_3$OD) δ 9.01 (dd, J = 1.76, 4.40 Hz, 1H), 8.33 (dd, J = 1.76, 8.51 Hz, 1H), 7.87 (d, J = 7.04 Hz, 1H), 7.55 (d, J = 3.52 Hz, 1H), 7.53 (t, J = 2.05 Hz, 1H), 7.35 (s, 4H), 4.74 (s, 2H), 3.26 (t, J = 6.16 Hz, 2H), 2.72 (t, J = 7.90 Hz, 2H), 2.56 (t, J = 6.16 Hz, 2H), 1.67-1.72 (m, 2H), 1.34-1.43 (m, 6H), 0.92 (t, J = 7.30 Hz, 3H) |

TABLE 5-continued

| Comp. No. | IUPAC name Structure | Starting material | $^1$H NMR δ (ppm) |
|---|---|---|---|
| 8 | (3-{[(5-{4-[3-(2-methylphenyl)propyl]phenyl}quinolin-8-yl)methyl]amino}propyl) phosphonic acid 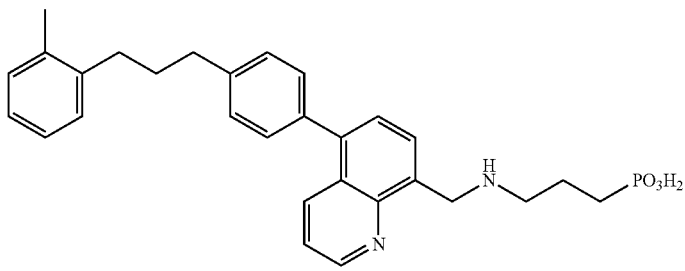 | Intermediate 25 | $^1$H NMR (600 MHz, CD$_3$OD) δ 8.98 (dd, J = 1.61, 4.26 Hz, 1H), 8.33 (dd, J = 1.47, 8.51 Hz, 1H), 7.92 (d, J = 7.34 Hz, 1H), 7.52-7.55 (m, 2H), 7.36-7.39 (m, 4H), 7.04-7.14 (m, 4H), 4.74 (s, 2H), 3.16 (t, J = 7.60 Hz, 2H), 2.79 (t, J = 8.20 Hz, 2H), 2.69 (t, J = 7.60 Hz, 2H), 2.27 (s, 3H), 2.00-2.07 (m, 2H), 1.92-1.98 (m, 2H), 1.63-1.73 (m, 2H) |
| 9 | [3-({[5-(2-fluoro-4-heptylphenyl)quinolin-8-yl]methyl}amino)propyl] phosphonic acid 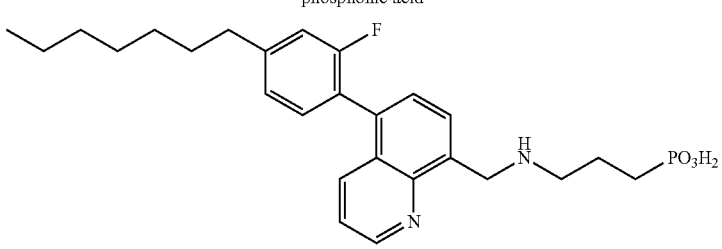 | Intermediate 26 | $^1$H NMR (CD$_3$OD) δ: 9.01 (dd, J = 4.1, 1.8 Hz, 1H), 8.09 (dt, J = 8.5, 1.9 Hz, 1H), 7.97 (d, J = 7.3 Hz, 1H), 7.54-7.61 (m, 2H), 7.32 (t, J = 7.8 Hz, 1H), 7.19 (dd, J = 8.2, 1.5 Hz, 1H), 7.13 (d, J = 11.2 Hz, 1H), 4.78 (d, J = 6.5 Hz, 2H), 3.21 (t, J = 6.6 Hz, 2H), 2.74 (t, J = 7.6 Hz, 2H), 2.05 (ddd, J = 17.5, 7.0, 6.9 Hz, 2H), 1.69-1.74 (m, 4H), 1.31-1.43 (m, 8H), 0.92 (t, J = 6.9 Hz, 3H) |
| 10 | [3-({[5-(3-fluoro-4-heptylphenyl)quinolin-8-yl]methyl}amino)propyl] phosphonic acid 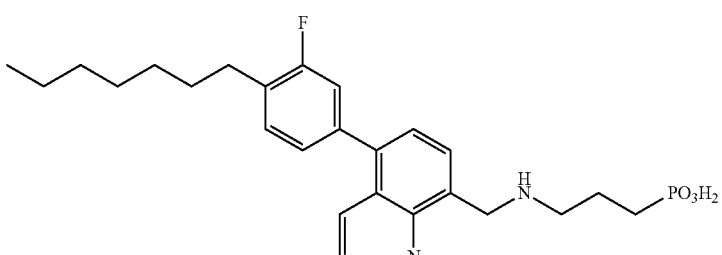 | Intermediate 27 | $^1$H NMR (CD$_3$OD) δ: 8.98 (dd, J = 4.3, 1.6 Hz, 1H), 8.27 (dd, J = 8.5, 1.5 Hz, 2H), 7.95 (d, J = 7.3 Hz, 1H), 7.52 (dd, J = 8.5, 3.8 Hz, 1H), 7.50 (d, J = 7.3 Hz, 1H), 7.35 (t, J = 7.8 Hz, 1H), 7.12 (dd, J = 7.6, 1.5 Hz, 1H), 7.07 (dd, J = 10.4, 1.3 Hz, 1H), 4.73 (s, 2H), 3.16 (t, J = 6.6 Hz, 2H), 2.71 (t, J = 7.6 Hz, 2H), 2.03-2.10 (m, 2H), 1.64-1.73 (m, 4H), 1.28-1.46 (m, 8H), 0.90 (t, J = 7.0 Hz, 3H) |

| Comp. No. | IUPAC name Structure | Starting material | $^1$H NMR δ (ppm) |
|---|---|---|---|
| 11 | {3-[({5-[4-(3-ethylheptyl)phenyl]quinolin-8-yl}methyl)amino]propyl} phosphonic acid | Intermediate 28 | $^1$H NMR (CD$_3$OD) δ: 8.98 (dd, J = 4.1, 1.5 Hz, 1H), 8.31 (dd, J = 8.5, 1.8 Hz, 1H), 7.93 (d, J = 7.3 Hz, 1H), 7.51-7.53 (m, 2H), 7.33 (s, 4H), 4.74 (s, 2H), 3.17 (t, J = 6.6 Hz, 2H), 2.69 (dd, J = 9.2, 5.7 Hz, 2H), 2.01-2.08 (m, 2H), 1.63-1.70 (m, 4H), 1.29-1.37 (m, 9H), 0.90-0.94 (m, J = 7.0, 7.0 Hz, 3H), 0.91 (t, J = 7.3 Hz, 3H) |
| 12 | [3-({[5-(4-octylphenyl)quinolin-8-yl]methyl}amino)propyl] phosphonic acid | Intermediate 29 | $^1$H NMR (CD$_3$OD) δ: 8.99 (dd, J = 4.3, 1.6 Hz, 1H), 8.35 (dd, J = 8.7, 1.6 Hz, 1H), 7.93 (d, J = 7.3 Hz, 1H), 7.54-7.57 (m, 2H), 7.36 (s, 4H), 4.75 (s, 2H), 3.18 (t, J = 6.5 Hz, 2H), 2.70-2.73 (m, 2H), 2.00-2.07 (m, 2H), 1.63-1.74 (m, 4H), 1.28-1.44 (m, 10H), 0.90 (t, J = 6.7 Hz, 3H) |
| 13 | [3-({[5-(3-fluoro-4-hexylphenyl)quinolin-8-yl]methyl}amino)propyl] phosphonic acid | Intermediate 37 | $^1$H NMR (CD$_3$OD) δ: 9.01 (dd, J = 4.1, 1.5 Hz, 1H), 8.34 (dd, J = 8.7, 1.6 Hz, 1H), 7.94 (d, J = 7.0 Hz, 1H), 7.55-7.59 (m, 2H), 7.39-7.42 (m, 1H), 7.14-7.20 (m, 2H), 4.76 (s, 2H), 3.18 (t, J = 6.6 Hz, 2H), 2.75 (t, J = 7.8 Hz, 2H), 2.01-2.08 (m, 2H), 1.65-1.74 (m, 4H), 1.33-1.44 (m, 6H), 0.90-0.94 (m, 3H) |
| 14 | {3-[({5-[4-(2-cyclohexylethyl)phenyl]quinolin-8-yl}methyl)amino]propyl} phosphonic acid | Intermediate 31 | $^1$H NMR (CD$_3$OD) δ: 9.00 (dd, J = 4.1, 1.5 Hz, 1H), 8.36 (dd, J = 8.5, 1.5 Hz, 1H), 7.93 (d, J = 7.0 Hz, 1H), 7.55-7.57 (m, 2H), 7.36 (s, 4H), 4.77 (s, 2H), 3.21 (t, J = 6.6 Hz, 2H), 2.72-2.75 (m, 2H), 2.01-2.09 (m, 2H), 1.84 (d, J = 11.4 Hz, 2H), 1.66-1.76 (m, 5H), 1.57-1.61 (m, 2H), 1.18-1.37 (m, 4H), 1.00 (qd, J = 12.3, 3.2 Hz, 2H) |

TABLE 5-continued

| Comp. No. | IUPAC name Structure | Starting material | ¹H NMR δ (ppm) |
|---|---|---|---|
| 15 | 2-({[5-(4-hexylphenyl)quinolin-8-yl]methyl}amino)ethanol 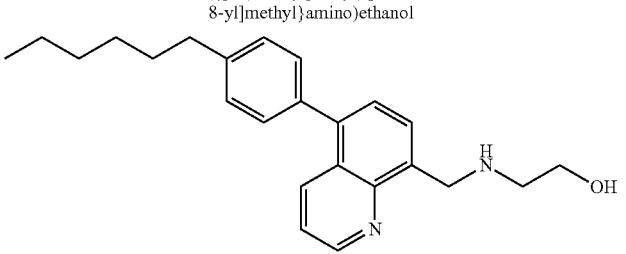 | Intermediate 36 | ¹H NMR (CDCl₃) δ: 8.91 (dd, J = 4.1, 1.5 Hz, 1H), 8.29 (dd, J = 8.5, 1.8 Hz, 1H), 7.69 (d, J = 7.3 Hz, 1H), 7.44 (d, J = 7.0 Hz, 1H), 7.37 (dd, J = 8.5, 4.1 Hz, 1H), 7.30-7.35 (m, 4H), 4.40 (s, 2H), 3.77 (t, J = 3.8 Hz, 2H), 2.91 (t, J = 5.0 Hz, 2H), 2.70 (t, J = 7.9 Hz, 2H), 1.70 (dt, J = 15.3, 7.6 Hz, 2H), 1.38-1.44 (m, 2H), 1.32-1.38 (m, 3H), 1.25 (br. s., 1H), 0.91 (t, J = 7.0 Hz, 3H) |
| 16 | (3-{[(5-{3-fluoro-4-[3-(2-methylphenyl)propyl]phenyl}quinolin-8-yl)methyl]amino}propyl)phosphonic acid 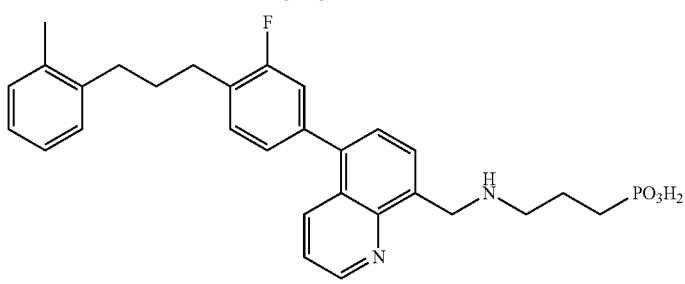 | Intermediate 33 | ¹H NMR (CD₃OD) δ: 9.00 (dd, J = 4.1, 1.8 Hz, 1H), 8.27-8.36 (m, 1H), 7.94 (d, J = 7.3 Hz, 1H), 7.54-7.59 (m, 2H), 7.42 (t, J = 7.9 Hz, 1H), 7.05-7.21 (m, 6H), 4.72 (s, 2H), 3.14 (t, J = 6.3 Hz, 2H), 2.82 (t, J = 7.6 Hz, 2H), 2.68-2.74 (m, 2H), 2.28 (s, 3H), 1.89-2.08 (m, 4H), 1.69 (dt, J = 17.2, 6.9 Hz, 2H) |
| 17 | (3-{[(5-{3-fluoro-4-[3-(3-methylphenyl)propyl]phenyl}quinolin-8-yl)methyl]amino}propyl)phosphonic acid 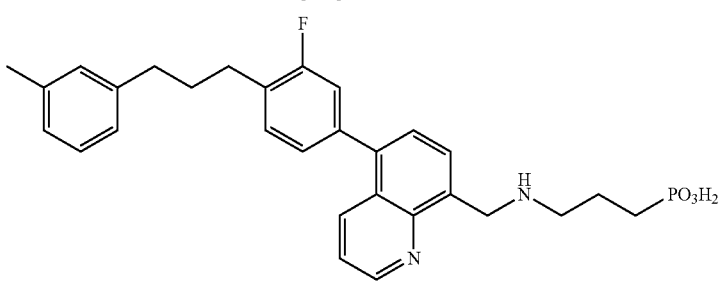 | Intermediate 30 | ¹H NMR (CD₃OD) δ: 9.01 (dd, J = 4.2, 1.6 Hz, 1H), 8.35 (dd, J = 8.6, 1.6 Hz, 1H), 7.94 (d, J = 7.6 Hz, 1H), 7.56-7.61 (m, 2H), 7.41 (t, J = 7.6 Hz, 1H), 7.12-7.22 (m, 3H), 6.96-7.04 (m, 3H), 4.76 (s, 2H), 3.19 (t, J = 6.6 Hz, 2H), 2.77 (t, J = 7.5 Hz, 2H), 2.68 (t, J = 7.6 Hz, 2H), 2.31 (s, 3H), 1.94-2.12 (m, 4H), 1.71 (ddd, J = 17.4, 7.0, 6.9 Hz, 2H) |

TABLE 5-continued

| Comp. No. | IUPAC name Structure | Starting material | ¹H NMR δ (ppm) |
|---|---|---|---|
| 18 | (3-{[(5-{3-fluoro-4-[3-(4-methylphenyl)propyl]phenyl}quinolin-8-yl)methyl]amino}propyl) phosphonic acid | Intermediate 34 | ¹H NMR (CD$_3$OD) δ: 9.00 (dd, J = 4.2, 1.6 Hz, 1H), 8.33 (dd, J = 8.6, 1.6 Hz, 1H), 7.94 (d, J = 7.3 Hz, 1H), 7.52-7.59 (m, 2H), 7.34-7.41 (m, 1H), 7.05-7.19 (m, 6H), 4.76 (s, 2H), 3.20 (t, J = 6.6 Hz, 2H), 2.62-2.78 (m, 4H), 2.28 (s, 3H), 1.91-2.13 (m, 4H), 1.71 (ddd, J = 17.4, 7.0, 6.9 Hz, 2H) |
| 19 | {3-[({5-[4-(3-ethylheptyl)-3-fluorophenyl]quinolin-8-yl}methyl)amino]propyl} phosphonic acid | Intermediate 38 | ¹H NMR (CD$_3$OD) δ: 9.00 (dd, J = 4.2, 1.6 Hz, 1H), 8.31 (dd, J = 8.5, 1.8 Hz, 1H), 7.95 (d, J = 7.3 Hz, 1H), 7.53-7.57 (m, 1H), 7.54 (d, J = 7.0 Hz, 1H), 7.38 (t, J = 7.8 Hz, 1H), 7.09-7.18 (m, 2H), 4.75 (s, 2H), 3.19 (t, J = 6.6 Hz, 2H), 2.67-2.75 (m, 2H), 2.06 (dqd, J = 16.7, 7.0, 6.4 Hz, 2H), 1.59-1.77 (m, 4H), 1.28-1.46 (m, 9H), 0.92 (t, J = 7.0 Hz, 3H), 0.91 (t, J = 7.2 Hz, 3H |
| 20 | {3-[({5-[4-(2-cyclohexylethyl)-3-fluorophenyl]quinolin-8-yl}methyl)amino]propyl} phosphonic acid | Intermediate 32 | ¹H NMR (CD$_3$OD) δ: 9.01 (dd, J = 4.4, 1.8 Hz, 1H), 8.33 (dd, J = 8.5, 1.8 Hz, 1H), 7.94 (d, J = 7.3 Hz, 1H), 7.55-7.60 (m, 2H), 7.40 (t, J = 7.9 Hz, 1H), 7.15-7.20 (m, J = 9.2, 1.3 Hz, 1H), 7.15 (dd, J = 13.8, 1.5 Hz, 1H), 4.76 (s, 2H), 3.19 (t, J = 6.6 Hz, 2H), 2.72-2.78 (m, 2H), 2.05 (dqd, J = 17.3, 7.0, 6.4 Hz, 2H), 1.84 (d, J = 12.6 Hz, 2H), 1.71 (dt, J = 17.2, 6.9 Hz, 5H), 1.57 (dt, J = 8.8, 7.0 Hz, 2H), 1.17-1.37 (m, 4H), 0.93-1.07 (m, 2H) |

TABLE 5-continued

| Comp. No. | IUPAC name Structure | Starting material | $^1$H NMR δ (ppm) |
|---|---|---|---|
| 22 | 2-[({5-[4-(3-ethylheptyl)-3-fluorophenyl]quinolin-8-yl}methyl)amino]ethanol 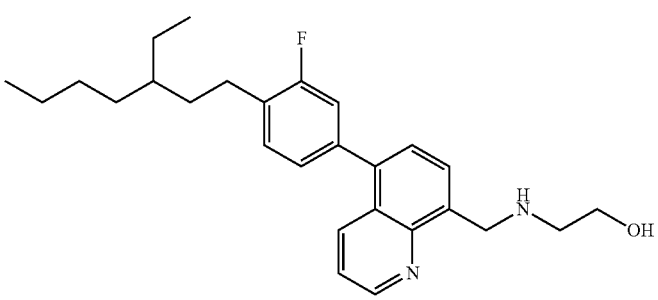 | Intermediate 38 | $^1$H NMR (600 MHz, CD$_3$OD) δ: 8.91-8.93 (m, 1H), 8.27-8.30 (m, 1H), 7.75-7.78 (m, 1H), 7.47-7.51 (m, 3H), 7.39 (s, 2H), 4.39 (d, J = 14.38 Hz, 2H), 3.70 (q, J = 5.60 Hz, 2H), 2.70-2.82 (m, 4H), 1.61-1.67 (m, 2H), 1.40-1.45 (m, 2H), 1.31-1.38 (m, 7H), 0.90-0.95 (m, 6H) |
| 23 | 2-[({5-[4-(3-ethylheptyl)-3-fluorophenyl]quinolin-8-yl}methyl)amino]ethyl dihydrogen phosphate 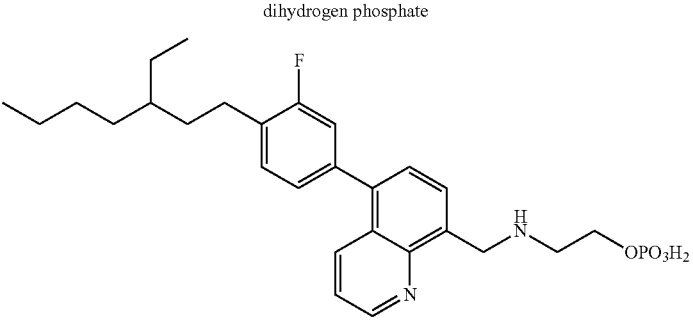 | Intermediate 38 | $^1$H NMR (600 MHz, CD$_3$OD) δ: 9.04 (dd, J = 1.61, 4.25 Hz, 1H), 8.42 (dd, J = 1.61, 8.66 Hz, 1H), 7.94 (d, J = 7.34 Hz, 1H), 7.63 (dd, J = 4.11, 8.51 Hz, 1H), 7.62 (d, J = 7.34 Hz, 1H), 7.42 (t, J = 7.78 Hz, 1H), 7.22 (dd, J = 1.61, 7.78 Hz, 1H), 7.18 (dd, J = 1.76, 10.56 Hz, 1H), 4.88 (s, 2H), 4.32-4.35 (m, 2H), 3.46 (dd, J = 4.26, 5.14 Hz, 2H), 2.74 (dd, J = 6.46, 9.68 Hz, 2H), 1.65 (dt, J = 5.30, 9.68 Hz, 2H), 1.41-1.45 (m, 2H), 1.31-1.40 (m, 7H), 0.93 (t, J = 7.60 Hz, 3H), 0.93 (t, J = 7.30 Hz, 3H) |

Example 9

Biological Data

Compounds were synthesized and tested for S1P1 activity using the GTP γ$^{35}$S binding assay. These compounds may be assessed for their ability to activate or block activation of the human S1P1 receptor in cells stably expressing the S1P1 receptor.

GTP γ$^{35}$S binding was measured in the medium containing (mM) HEPES 25, pH 7.4, MgCl$_2$ 10, NaCl 100, dithitothreitol 0.5, digitonin 0.003%, 0.2 nM GTP γ$^{35}$S, and 5 μg membrane protein in a volume of 150 μl. Test compounds were included in the concentration range from 0.08 to 5,000 nM unless indicated otherwise. Membranes were incubated with 100 μM 5'-adenylylimmidodiphosphate for 30 min, and subsequently with 10 μM GDP for 10 min on ice. Drug solutions and membrane were mixed, and then reactions were initiated by adding GTP γ$^{35}$S and continued for 30 min at 25° C. Reaction mixtures were filtered over Whatman GF/B filters under vacuum, and washed three times with 3 mL of ice-cold buffer (HEPES 25, pH7.4, MgCl$_2$ 10 and NaCl 100). Filters were dried and mixed with scintillant, and counted for $^{35}$S activity using a β-counter. Agonist-induced GTP γ$^{35}$S binding was obtained by subtracting that in the absence of agonist.

Binding data were analyzed using a non-linear regression method. In case of antagonist assay, the reaction mixture contained 10 nM S1P1 in the presence of test antagonist at concentrations ranging from 0.08 to 5000 nM.

Table 6 shows activity potency: S1P1 receptor from GTP γ$^{35}$S: nM, (EC$_{50}$)

TABLE 6

| IUPAC name | S1P1 EC$_{50}$ (nM) |
|---|---|
| [3-({[4-(4-hexylphenyl)-1-naphthyl]methyl}amino)propyl] phosphonic acid | 54.2 |
| [3-({[5-(4-hexylphenyl)quinolin-8-yl]methyl}amino)propyl]phosphonic acid | 0.6 |
| 2-({[5-(4-hexylphenyl)quinolin-8-yl]methyl}amino)ethyl dihydrogen phosphate | 31.1 |
| 3-({[5-(4-hexylphenyl)quinolin-8-yl]methyl}amino)propanoic acid | 872 |
| {3-[({5-[4-(3-phenylpropyl)phenyl]quinolin-8-yl}methyl)amino]propyl}phosphonic acid | 8.3 |
| (3-{[({5-[4-[3-(2-methylphenyl)propyl]phenyl]quinolin-8-yl}methyl) amino} propyl) phosphonic acid | 3.8 |
| [3-({[5-(4-hexylphenyl)quinolin-8-yl]methyl}amino)butyl]phosphonic acid | 61.7 |
| {3-[({5-[3-fluoro-4-(3-phenylpropyl)phenyl]quinolin-8-yl}methyl)amino]propyl}phosphonic acid | 5.95 |

TABLE 6-continued

| IUPAC name | S1P1 EC$_{50}$ (nM) |
|---|---|
| [3-({[5-(2-fluoro-4-heptylphenyl)quinolin-8-yl]methyl}amino)propyl]phosphonic acid | 13.6 |
| [3-({[5-(3-fluoro-4-heptylphenyl)quinolin-8-yl]methyl}amino)propyl]phosphonic acid | 223 |
| {3-[({5-[4-(3-ethylheptyl)phenyl]quinolin-8-yl}methyl)amino]propyl}phosphonic acid | 6.97 |
| [3-({[5-(4-octylphenyl)quinolin-8-yl]methyl}amino)propyl]phosphonic acid | 11.2 |
| [3-({[5-(3-fluoro-4-hexylphenyl)quinolin-8-yl]methyl}amino)propyl]phosphonic acid | 1.3 |
| {3-[({5-[4-(2-cyclohexylethyl)phenyl]quinolin-8-yl}methyl)amino]propyl}phosphonic acid | 1.5 |
| 2-({[5-(4-hexylphenyl)quinolin-8-yl]methyl}amino)ethanol | 192 |
| (3-{[(5-{3-fluoro-4-[3-(2-methylphenyl)propyl]phenyl}quinolin-8-yl)methyl]amino}propyl)phosphonic acid | 1.0 |
| (3-{[(5-{3-fluoro-4-[3-(3-methylphenyl)propyl]phenyl}quinolin-8-yl)methyl]amino}propyl)phosphonic acid | 0.3 |
| (3-{[(5-{3-fluoro-4-[3-(4-methylphenyl)propyl]phenyl}quinolin-8-yl)methyl]amino}propyl)phosphonic acid | 1 |
| {3-[({5-[4-(3-ethylheptyl)-3-fluorophenyl]quinolin-8-yl}methyl)amino]propyl}phosphonic acid | 2.5 |
| {3-[({5-[4-(2-cyclohexylethyl)-3-fluorophenyl]quinolin-8-yl}methyl)amino]propyl}phosphonic acid | 1.68 |
| 2-[({5-[4-(3-ethylheptyl)-3-fluorophenyl]quinolin-8-yl}methyl)amino]ethyl dihydrogen phosphate | 2.63 |
| 2-[({5-[4-(3-ethylheptyl)-3-fluorophenyl]quinolin-8-yl}methyl)amino]ethanol | 137 |

Example 10

Lymphopenia Assay in Mice

Test drugs are prepared in a solution containing 3% (w/v) 2-hydroxy propyl R-cyclodextrin (HPBCD) and 1% DMSO to a final concentration of 1 mg/ml, and subcutaneously injected to female C57BL6 mice (CHARLES RIVERS) weighing 20-25 g at the dose of 10 mg/Kg. Blood samples are obtained by puncturing the submandibular skin with a Goldenrod animal lancet at 5, 24, 48, 72, and 96 hrs post drug application. Blood is collected into microvettes (SARSTEDT) containing EDTA tripotassium salt. Lymphocytes in blood samples are counted using a HEMAVET Multispecies Hematology System, HEMAVET HV950FS (Drew Scientific Inc.). (Hale, J. et al Bioorg. & Med. Chem. Lett. 14 (2004) 3351).

Figure 2:
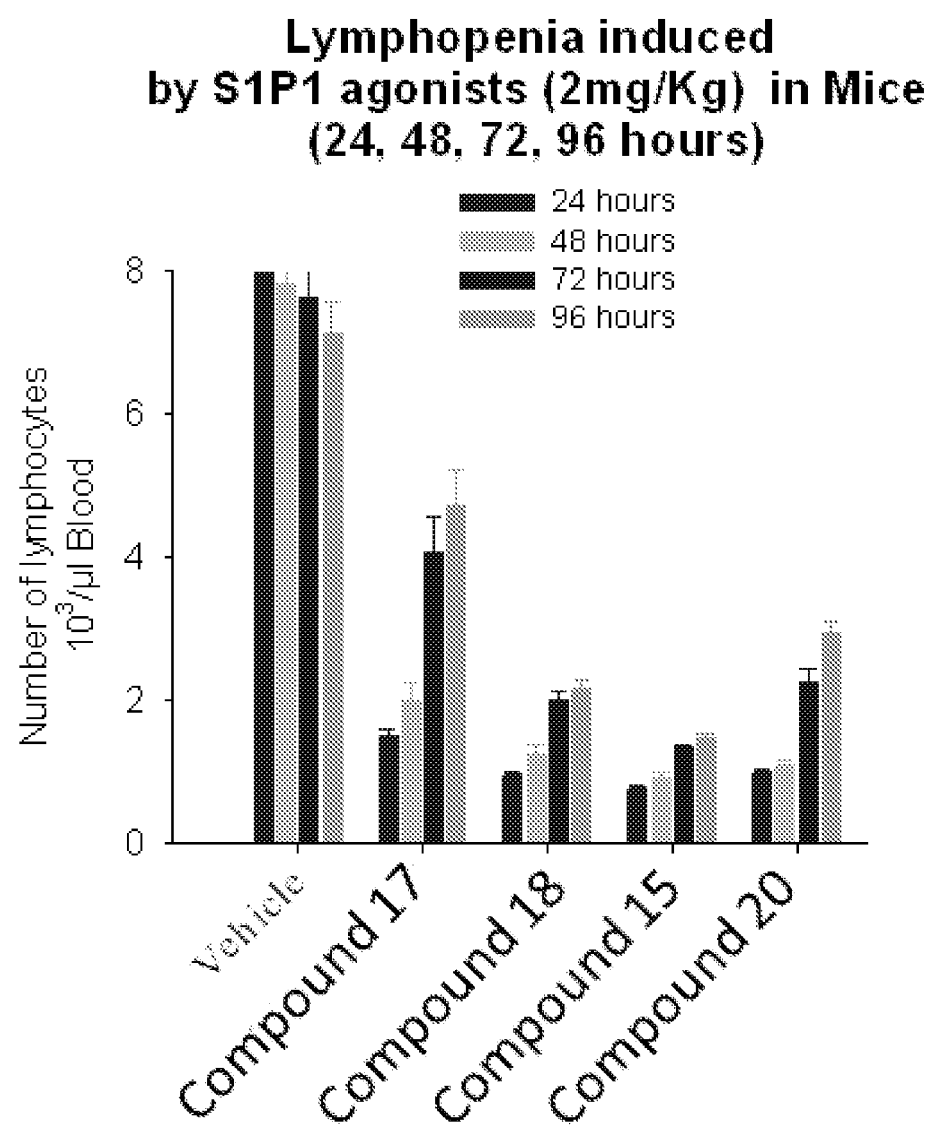
FIG. 2 shows that Compounds 15, 17, 18 and 20 lowered lymphocyte count after 24 hours in a lymphopenia assay in mice, by measuring the in vivo blood lymphocyte depletion after dosing.

A lymphopenia assay in mice, as previously described, was employed to measure the in vivo blood lymphocyte depletion after dosing Compounds 9, 10, 11 and 14, (FIG. 1) and Compounds 15, 17, 18 and 20, (FIG. 2). These S1P agonists (or modulators) are useful for S1P-related diseases, and exemplified by the lymphopenia in vivo response. In general, test compounds were prepared in a solution containing 3% (w/v) 2-hydroxy propyl β-cyclodextrin (HPBCD) and 1% DMSO to a final concentration of 1 mg/ml, and subcutaneously injected to female C57BL6 mice (CHARLES RIVERS) weighing 20-25 g at the dose of 10 mg/Kg or 2 mg/Kg. Blood samples were obtained by puncturing the submandibular skin with a Goldenrod animal lancet at 24, 48, 72 and 96 hrs post drug application. Blood was collected into microvettes (SARSTEDT) containing EDTA tripotassium salt. Lymphocytes in blood samples were counted using a HEMAVET Multispecies Hematology System, HEMAVET HV950FS (Drew Scientific Inc.). Results are shown in FIGS. 1 and 2 that depict lowered lymphocyte count after 24 hours (<1 number of lymphocytes 10$^3$/μL blood).

What is claimed is:

1. A method of treating an immunosuppressant disorder associated with the sphingosine-1-phosphate receptor modulation, wherein the immunosuppressant disorder is selected from: rheumatoid arthritis, psoriasis, atherosclerosis, autoimmune uveitis, dry eye, inflammatory bowel diseases, atopic allergy, atopic dermatitis, contact dermatitis, multiple sclerosis, Sjogren's syndrome and organ transplant rejection, in a mammal in need thereof, which comprises administering to a mammal in need thereof, a pharmaceutical composition comprising a therapeutically effective amount of at least one compound represented by Formula I or a pharmaceutically acceptable salt thereof:

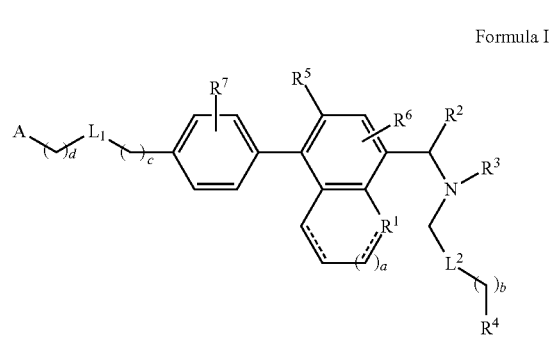

Formula I wherein:

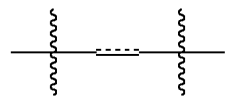

represents a single

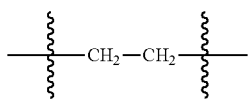 [SMILES: *CC*]

or a double bond

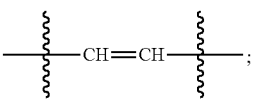 [SMILES: *C=C*]

;

A is substituted or unsubstituted aryl, substituted or unsubstituted heterocycle, substituted or unsubstituted $C_{5-6}$ cycloalkyl, substituted or unsubstituted $C_{5-8}$ cycloalkenyl, or hydrogen;

$R^2$ is hydrogen, halogen, —$OC_{1-3}$ alkyl, substituted or unsubstituted $C_{1-3}$ alkyl, CN, C(O)$R^8$, $NR^9R^{10}$ or hydroxyl;

$R^3$ is hydrogen, halogen, substituted or unsubstituted $C_{1-3}$ alkyl, C(O)$R^8$ or hydroxyl;

$R^4$ is OPO$_3$H$_2$, carboxylic acid, PO$_3$H$_2$, substituted or unsubstituted $C_{1-6}$ alkyl, —S(O)$_2$H, —P(O)MeOH, —P(O)(H)OH or OR$^{11}$;

$R^5$ is H, halogen, —$OC_{1-3}$ alkyl, substituted or unsubstituted $C_{1-3}$ alkyl, CN, C(O)$R^8$, $NR^9R^{10}$ or hydroxyl;

$R^6$ is H, halogen, —$OC_{1-3}$ alkyl, substituted or unsubstituted $C_{1-3}$ alkyl, CN, C(O)$R^8$, $NR^9R^{10}$ or hydroxyl;

$R^7$ is H, halogen, —$OC_{1-3}$ alkyl, substituted or unsubstituted $C_{1-3}$ alkyl, CN, $C(O)R^8$, $NR^9R^{10}$ or hydroxyl;

$R^8$ is H, $OR^{11}$ or substituted or unsubstituted $C_{1-3}$ alkyl;

$R^9$ is H or substituted or unsubstituted $C_{1-3}$ alkyl;

$R^{10}$ is H or substituted or unsubstituted $C_{1-3}$ alkyl;

$R^{11}$ is H or substituted or unsubstituted $C_{1-3}$ alkyl;

$L^1$ is O, S, NH or $CHR^{12}$;

$L^2$ is O, S, NH or $CHR^{13}$;

$R^{12}$ is H or substituted or unsubstituted $C_{1-3}$ alkyl;

$R^{13}$ is H or substituted or unsubstituted $C_{1-3}$ alkyl;

a is 1;

b is 0, 1, 2 or 3;

c is 0, 1, 2, 3 or 4;

d is 1, 2, 3 or 4;

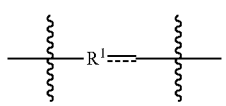

represents

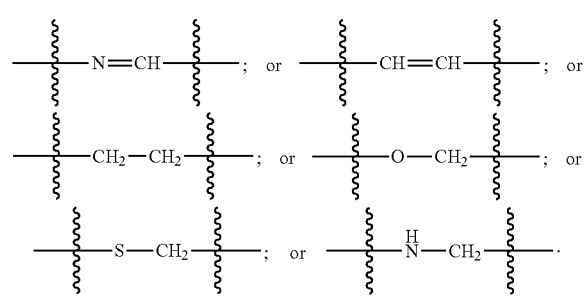

2. The method according to claim 1, wherein the mammal is a human.

3. The method according to claim 1, wherein:

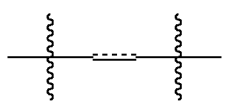

represents a double bond

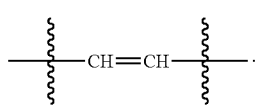

4. The method according to claim 1, wherein:

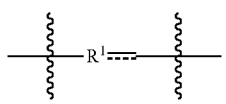

represents

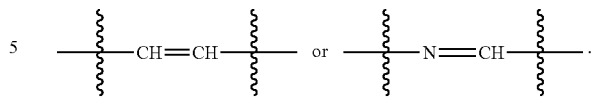

5. The method according to claim 1, wherein:

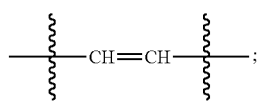

represents a double bond

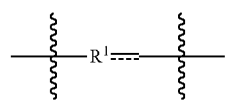

and

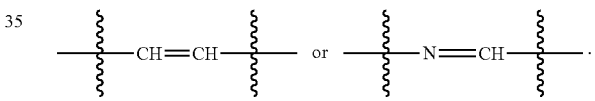

represents

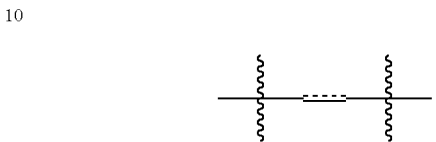

6. The method according to claim 1, wherein:
A is hydrogen.

7. The method according to claim 1, wherein:
A is substituted or unsubstituted aryl.

8. The method according to claim 1, wherein:

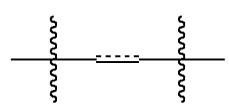

represents a double bond

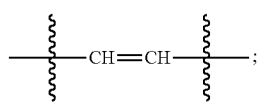

A is substituted or unsubstituted aryl; and

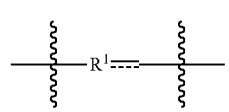

represents

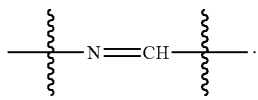

9. The method according to claim 1, wherein:

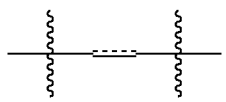

represents a double bond

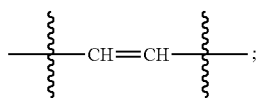 [SMILES: *C=C* ; ";"]

A is hydrogen; and

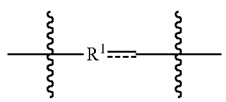

represents

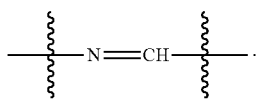

10. The method according to claim 1, wherein the compound of Formula I is selected from:
[3-({[5-(4-hexylphenyl)quinolin-8-yl]methyl}amino)propyl]phosphonic acid;
[3-({[4-(4-hexylphenyl)-1-naphthyl]methyl}amino)propyl]phosphonic acid;
2-({[5-(4-hexylphenyl)quinolin-8-yl]methyl}amino)ethyl dihydrogen phosphate;
3-({[5-(4-hexylphenyl)quinolin-8-yl]methyl}amino)propanoic acid;
{3-[({5-[4-(3-phenylpropyl)phenyl]quinolin-8-yl}methyl)amino]propyl}phosphonic acid;
(3-{[(5-{4-[3-(2-methylphenyl)propyl]phenyl}quinolin-8-yl)methyl]amino}propyl)phosphonic acid;
[3-({[5-(4-hexylphenyl)quinolin-8-yl]methyl}amino)butyl]phosphonic acid;
{3-[({5-[3-fluoro-4-(3-phenylpropyl)phenyl]quinolin-8-yl}methyl)amino]propyl}phosphonic acid;
[3-({[5-(2-fluoro-4-heptylphenyl)quinolin-8-yl]methyl}amino)propyl]phosphonic acid;
[3-({[5-(3-fluoro-4-heptylphenyl)quinolin-8-yl]methyl}amino)propyl]phosphonic acid;
{3-[({5-[4-(3-ethylheptyl)phenyl]quinolin-8-yl}methyl)amino]propyl}phosphonic acid;
[3-({[5-(4-octylphenyl)quinolin-8-yl]methyl}amino)propyl]phosphonic acid;
[3-({[5-(3-fluoro-4-hexylphenyl)quinolin-8-yl]methyl}amino)propyl]phosphonic acid;
{3-[({5-[4-(2-cyclohexylethyl)phenyl]quinolin-8-yl}methyl)amino]propyl}phosphonic acid;
2-({[5-(4-hexylphenyl)quinolin-8-yl]methyl}amino)ethanol;
(3-{[(5-{3-fluoro-4-[3-(2-methylphenyl)propyl]phenyl}quinolin-8-yl)methyl]amino}propyl)phosphonic acid;
(3-{[(5-{3-fluoro-4-[3-(3-methylphenyl)propyl]phenyl}quinolin-8-yl)methyl]amino}propyl)phosphonic acid;
(3-{[(5-{3-fluoro-4-[3-(4-methylphenyl)propyl]phenyl}quinolin-8-yl)methyl]amino}propyl)phosphonic acid;
{3-[({5-[4-(3-ethylheptyl)-3-fluorophenyl]quinolin-8-yl}methyl)amino]propyl}phosphonic acid;
{3-[({5-[4-(2-cyclohexylethyl)-3-fluorophenyl]quinolin-8-yl}methyl)amino]propyl}phosphonic acid;
2-[({5-[4-(3-ethylheptyl)-3-fluorophenyl]quinolin-8-yl}methyl)amino]ethanol; and
2-[({5-[4-(3-ethylheptyl)-3-fluorophenyl]quinolin-8-yl}methyl)amino]ethyl dihydrogen phosphate.

\* \* \* \* \*

UNITED STATES PATENT AND TRADEMARK OFFICE
CERTIFICATE OF CORRECTION

PATENT NO. : 8,653,050 B2
APPLICATION NO. : 13/936891
DATED : February 18, 2014
INVENTOR(S) : Janet A. Takeuchi et al.

It is certified that error appears in the above-identified patent and that said Letters Patent is hereby corrected as shown below:

On the title page, in item (56), under "Other Publications", in column 2, line 2, delete "Sterochemistry" and insert -- Stereochemistry, --, therefor.

On the title page, in item (56), under "Other Publications", in column 2, line 6, delete "SIP3" and insert -- S1P3 --, therefor.

In the Specification:

In column 1, line 26, delete "Sphingosine-1 phosphate" and insert -- Sphingosine-1-phosphate --, therefor.

In column 3, line 56, delete "$C_{6-6}$" and insert -- $C_{5-8}$ --, therefor.

In column 9, line 19, delete "$C_{6-6}$" and insert -- $C_{5-8}$ --, therefor.

In column 16, line 65, delete "$C_{6-8}$" and insert -- $C_{5-8}$ --, therefor.

In column 17, line 64, delete "form" and insert -- from --, therefor.

In column 18, line 25, delete ""—C(O)ON"." and insert -- "—C(O)OH". --, therefor.

In column 19, line 47, delete "Stahal" and insert -- Stahl --, therefor.

In column 19, line 48, delete "Chemica" and insert -- Chimica --, therefor.

In column 19, line 56, delete "Stahal" and insert -- Stahl --, therefor.

In column 19, line 57, delete "Chemica" and insert -- Chimica --, therefor.

In column 20, line 40, delete "antoimmune" and insert -- autoimmune --, therefor.

In column 20, line 42, delete "dermititis," and insert -- dermatitis, --, therefor.

In column 21, lines 20-21, delete "antoimmune" and insert -- autoimmune --, therefor.

In column 21, line 22, delete "dermititis," and insert -- dermatitis, --, therefor.

In column 24, line 41, delete "trifluorocaetic" and insert -- trifluoroacetic --, therefor.

In column 24, line 43, delete "bromoquinolone" and insert -- bromoquinoline --, therefor.

Signed and Sealed this
Twenty-seventh Day of May, 2014

Michelle K. Lee
*Deputy Director of the United States Patent and Trademark Office*

In column 24, lines 46-47, delete "naphthylmethyester" and insert -- naphthylmethylester --, therefor.

In column 25, line 40, delete "diasteroisomeric" and insert -- diastereoisomeric --, therefor.

In column 25, line 45, delete "SP1." and insert -- S1P. --, therefor.

In column 25, line 60, delete "AM FineCom," and insert -- AMFineCom, --, therefor.

In column 28, line 37, delete "queneched" and insert -- quenched --, therefor.

In column 28, line 42, delete "as" and insert -- 5 as --, therefor.

In column 31, lines 15-16 (TABLE 3), delete " 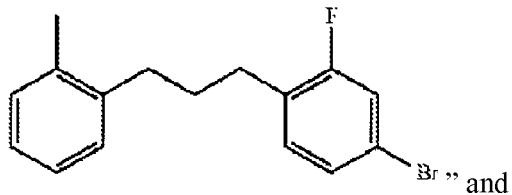 " and insert -- 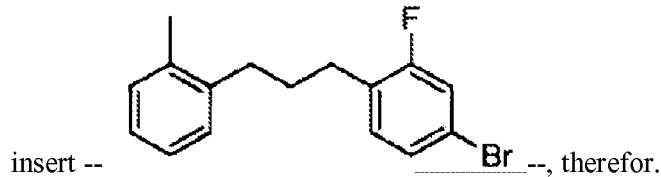 --, therefor.

In column 34, line 9 (TABLE 3), delete "Hz." and insert -- Hz, --, therefor.

In column 38, line 5 (TABLE 4), delete "hepylbenzene" and insert -- heptylbenzene --, therefor.

In column 40, line 46 (TABLE 4), delete "(m,4H)," and insert -- (m, 4H), --, therefor.

In column 42, line 21 (TABLE 4), delete "0.60." and insert -- 0.60, --, therefor.

In column 44, line 8 (TABLE 4), delete "Hz." and insert -- Hz, --, therefor.

In column 46, line 19, delete "though" and insert -- through --, therefor.

In column 48, line 29, delete "(tdd," and insert -- (dd, --, therefor.

In column 57, lines 52-53, delete "dithitothreitol" and insert -- dithiothreitol --, therefor.

In column 57, line 58, delete "5'-adenylylimmidodiphosphate" and insert -- 5'-adenylylimidodiphosphate --, therefor.

In column 59, line 35, delete "R-cyclodextrin" and insert -- β-cyclodextrin --, therefor.

In the Claims:

In column 60, line 54, in claim 1, delete "$C_{5-6}$" and insert -- $C_{5-8}$ --, therefor.